United States Patent [19]
Holton et al.

[11] Patent Number: 5,859,329
[45] Date of Patent: Jan. 12, 1999

[54] GENETIC SEQUENCES ENCODING FLAVONOL SYNTHASE ENZYMES AND USES THEREFOR

[75] Inventors: Timothy Albert Holton, Northcote; Lisa Ann Keam, North Fitzroy, both of Australia

[73] Assignee: International Flower Developments Pty. Ltd., Collingwood, Australia

[21] Appl. No.: 379,556

[22] PCT Filed: Aug. 5, 1993

[86] PCT No.: PCT/AU93/00400

§ 371 Date: Mar. 22, 1995

§ 102(e) Date: Mar. 22, 1995

[87] PCT Pub. No.: WO94/03606

PCT Pub. Date: Feb. 17, 1994

[30] Foreign Application Priority Data

Aug. 5, 1992 [AU] Australia ............................ PL3944/92

[51] Int. Cl.[6] .............................. A01H 4/00; C12N 15/82; C12N 15/29
[52] U.S. Cl. .................................. 800/205; 800/DIG. 43; 800/DIG. 67; 435/172.3; 435/320.1; 536/23.2
[58] Field of Search ............................ 800/205, DIG. 43, 800/67; 435/172.3, 320.1; 536/23.2, 24.3

[56] References Cited

U.S. PATENT DOCUMENTS 5,034,323  7/1991  Jorgensen et al. ................... 435/172.3
5,349,125  9/1994  Holton et al. ........................... 800/205

FOREIGN PATENT DOCUMENTS 0 335 451  10/1989  European Pat. Off. .

OTHER PUBLICATIONS

Mol et al., (1989), "Genetic Manipulation of Floral Pigmentation Genes," *Plant Molecular Biology* 13: 287–294.

Kochs et al., (1987), "Induction and Characterization of a NADPH–Dependent Flavone Synthase from Cell Cultures of Soybean," *Journal of Biosciences* 42: 343–348.

Tunen et al., (1988), "Cloning of the Two Chalcone Flavanone Isomerase Genes from *Petunia hybrida*: Coordinate, Light–Regulated and Differential Expression of Flavonoid Genes," *The EMBO Journal* 7(5): 1257–1263.

Stich et al., (1992), "Flavonal Synthase Activity and the Regulation of Flavonol and Anthocyanin Biosynthesis During Flower Development in *Dianthus caryophyllus* L. (Carnation)," *Journal of Biosciences* 47: 553–560.

*Primary Examiner*—Che S. Chereskin
*Attorney, Agent, or Firm*—Scully, Scott, Murphy & Presser

[57] ABSTRACT

The present invention relates generally to genetic sequences encoding flavonoid pathway metabolising enzymes and in particular enzymes having flavonol synthase activity and their use such as in manipulating production of pigmentory molecules in plants. More particularly, the present invention provides genetic sequences encoding flavonol synthase (FLS).

43 Claims, 5 Drawing Sheets

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 1211 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 59..1101

( x i ) SEQUENCE DESCRIPTION: SEQ ID NO:1:

```
GTTTTTCTAA AAACAGAGGG CCTAACTTCT GTATAGACAA AGAAAAAAAG AAAAGAAA                    58

ATG AAA ACA GCT CAA GGT GTC AGT GCA ACC CTA ACA ATG GAA GTG GCA                   106
Met Lys Thr Ala Gln Gly Val Ser Ala Thr Leu Thr Met Glu Val Ala
  1               5                  10                  15

AGA GTA CAA GCA ATA GCA TCG TTA AGC AAG TGC ATG GAC ACA ATT CCA                   154
Arg Val Gln Ala Ile Ala Ser Leu Ser Lys Cys Met Asp Thr Ile Pro
             20                  25                  30

TCA GAG TAC ATT AGG TCC GAG AAT GAG CAA CCA GCA GCC ACA ACC CTG                   202
Ser Glu Tyr Ile Arg Ser Glu Asn Glu Gln Pro Ala Ala Thr Thr Leu
         35                  40                  45

CAT GGG GTA GTT CTT CAA GTG CCA GTG ATT GAC CTA CGT GAC CCT GAT                   250
His Gly Val Val Leu Gln Val Pro Val Ile Asp Leu Arg Asp Pro Asp
     50                  55                  60

GAG AAC AAG ATG GTG AAG CTC ATA GCT GAT GCT AGC AAA GAG TGG GGG                   298
Glu Asn Lys Met Val Lys Leu Ile Ala Asp Ala Ser Lys Glu Trp Gly
 65                  70                  75                  80

ATA TTC CAA CTG ATC AAC CAT GGC ATT CCT GAT GAG GCT ATC GCG GAT                   346
Ile Phe Gln Leu Ile Asn His Gly Ile Pro Asp Glu Ala Ile Ala Asp
                 85                  90                  95

TTA CAG AAA GTA GGG AAA GAG TTC TTT GAA CAT GTT CCA CAG GAG GAG                   394
Leu Gln Lys Val Gly Lys Glu Phe Phe Glu His Val Pro Gln Glu Glu
            100                 105                 110

AAA GAG CTG ATT GCC AAG ACT CCA GGA TCA AAC GAC ATT GAA GGC TAT                   442
Lys Glu Leu Ile Ala Lys Thr Pro Gly Ser Asn Asp Ile Glu Gly Tyr
        115                 120                 125

GGA ACT TCT CTG CAG AAG GAA GTG GAA GGC AAG AAA GGT TGG GTG GAT                   490
Gly Thr Ser Leu Gln Lys Glu Val Glu Gly Lys Lys Gly Trp Val Asp
    130                 135                 140

CAT TTG TTC CAT AAG ATT TGG CCT CCT TCT GCC GTC AAC TAT CGT TAT                   538
His Leu Phe His Lys Ile Trp Pro Pro Ser Ala Val Asn Tyr Arg Tyr
145                 150                 155                 160

TGG CCT AAA AAC CCT CCT TCA TAC AGG GAA GCA AAC GAA GAA TAT GGA                   586
Trp Pro Lys Asn Pro Pro Ser Tyr Arg Glu Ala Asn Glu Glu Tyr Gly
                165                 170                 175

AAG AGG ATG CGA GAA GTT GTA GAC AGA ATT TTT AAG AGC TTG TCT CTT                   634
Lys Arg Met Arg Glu Val Val Asp Arg Ile Phe Lys Ser Leu Ser Leu
            180                 185                 190

GGG CTT GGG CTT GAA GGC CAT GAA ATG ATA GAG GCA GCT GGT GGT GAT                   682
Gly Leu Gly Leu Glu Gly His Glu Met Ile Glu Ala Ala Gly Gly Asp
        195                 200                 205
```

```
GAG  ATA  GTT  TAC  TTG  TTG  AAG  ATC  AAC  TAT  TAC  CCA  CCA  TGC  CCA  AGG      730
Glu  Ile  Val  Tyr  Leu  Leu  Lys  Ile  Asn  Tyr  Tyr  Pro  Pro  Cys  Pro  Arg
     210                      215                      220

CCC  GAT  TTG  GCT  CTT  GGT  GTT  GTG  GCC  CAT  ACG  GAC  ATG  TCA  TAT  ATC      778
Pro  Asp  Leu  Ala  Leu  Gly  Val  Val  Ala  His  Thr  Asp  Met  Ser  Tyr  Ile
225                      230                      235                      240

ACC  ATT  CTT  GTC  CCA  AAT  GAA  GTC  CAA  GGC  CTC  CAA  GTG  TTC  AAG  GAT      826
Thr  Ile  Leu  Val  Pro  Asn  Glu  Val  Gln  Gly  Leu  Gln  Val  Phe  Lys  Asp
                    245                      250                      255

GGC  CAT  TGG  TAT  GAT  GTC  AAG  TAC  ATA  CCA  AAT  GCC  TTA  ATT  GTC  CAT      874
Gly  His  Trp  Tyr  Asp  Val  Lys  Tyr  Ile  Pro  Asn  Ala  Leu  Ile  Val  His
               260                      265                      270

ATT  GGT  GAC  CAA  GTT  GAG  ATT  CTT  AGC  AAT  GGC  AAA  TAC  AAG  AGT  GTA      922
Ile  Gly  Asp  Gln  Val  Glu  Ile  Leu  Ser  Asn  Gly  Lys  Tyr  Lys  Ser  Val
          275                      280                      285

TAC  CAT  AGG  ACA  ACG  GTG  AAC  AAG  GAC  AAG  ACA  AGA  ATG  TCA  TGG  CCG      970
Tyr  His  Arg  Thr  Thr  Val  Asn  Lys  Asp  Lys  Thr  Arg  Met  Ser  Trp  Pro
     290                      295                      300

GTT  TTC  TTG  GAG  CCC  CCG  TCA  GAG  CAT  GAA  GTT  GGG  CCA  ATT  CCT  AAG     1018
Val  Phe  Leu  Glu  Pro  Pro  Ser  Glu  His  Glu  Val  Gly  Pro  Ile  Pro  Lys
305                      310                      315                      320

CTG  CTT  AGT  GAG  GCC  AAC  CCA  CCC  AAA  TTC  AAG  ACC  AAG  AAG  TAC  AAG     1066
Leu  Leu  Ser  Glu  Ala  Asn  Pro  Pro  Lys  Phe  Lys  Thr  Lys  Lys  Tyr  Lys
                    325                      330                      335

GAT  TAC  GTC  TAT  TGT  AAG  CTT  AAC  AAG  CTT  CCT  CA GTGAAGAAGC                1111
Asp  Tyr  Val  Tyr  Cys  Lys  Leu  Asn  Lys  Leu  Pro
340                      345

ACCTCTATGT  ATGGAGCGAT  TAGCTATATC  TTCGCGAGTG  TTATGGTTTT  ATTTGTACTG             1171

TCCTAATTAA  TTACACAAAA  AAAAAAAAAA  AAAAAAAAA                                      1211
```

( 2 ) INFORMATION FOR SEQ ID NO:2:

( i ) SEQUENCE CHARACTERISTICS:
        ( A ) LENGTH: 347 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Lys  Thr  Ala  Gln  Gly  Val  Ser  Ala  Thr  Leu  Thr  Met  Glu  Val  Ala
1                   5                        10                       15

Arg  Val  Gln  Ala  Ile  Ala  Ser  Leu  Ser  Lys  Cys  Met  Asp  Thr  Ile  Pro
               20                       25                       30

Ser  Glu  Tyr  Ile  Arg  Ser  Glu  Asn  Glu  Gln  Pro  Ala  Ala  Thr  Thr  Leu
          35                       40                       45

His  Gly  Val  Val  Leu  Gln  Val  Pro  Val  Ile  Asp  Leu  Arg  Asp  Pro  Asp
     50                       55                       60

Glu  Asn  Lys  Met  Val  Lys  Leu  Ile  Ala  Asp  Ala  Ser  Lys  Glu  Trp  Gly
65                       70                       75                       80

Ile  Phe  Gln  Leu  Ile  Asn  His  Gly  Ile  Pro  Asp  Glu  Ala  Ile  Ala  Asp
                    85                       90                       95

Leu  Gln  Lys  Val  Gly  Lys  Glu  Phe  Phe  Glu  His  Val  Pro  Gln  Glu  Glu
               100                      105                      110

Lys  Glu  Leu  Ile  Ala  Lys  Thr  Pro  Gly  Ser  Asn  Asp  Ile  Glu  Gly  Tyr
          115                      120                      125

Gly  Thr  Ser  Leu  Gln  Lys  Glu  Val  Glu  Gly  Lys  Lys  Gly  Trp  Val  Asp
     130                      135                      140

His  Leu  Phe  His  Lys  Ile  Trp  Pro  Pro  Ser  Ala  Val  Asn  Tyr  Arg  Tyr
```

|  |  |  |  | 145 |  |  |  |  | 150 |  |  |  |  | 155 |  |  |  |  | 160 |
|---|---|---|---|---|---|---|---|---|---|---|---|---|---|---|---|---|---|---|---|

Trp Pro Lys Asn Pro Pro Ser Tyr Arg Glu Ala Asn Glu Glu Tyr Gly
                165             170                 175

Lys Arg Met Arg Glu Val Val Asp Arg Ile Phe Lys Ser Leu Ser Leu
            180             185                 190

Gly Leu Gly Leu Glu Gly His Glu Met Ile Glu Ala Ala Gly Gly Asp
        195             200             205

Glu Ile Val Tyr Leu Leu Lys Ile Asn Tyr Tyr Pro Pro Cys Pro Arg
    210             215             220

Pro Asp Leu Ala Leu Gly Val Val Ala His Thr Asp Met Ser Tyr Ile
225             230             235             240

Thr Ile Leu Val Pro Asn Glu Val Gln Gly Leu Gln Val Phe Lys Asp
                245             250             255

Gly His Trp Tyr Asp Val Lys Tyr Ile Pro Asn Ala Leu Ile Val His
            260             265             270

Ile Gly Asp Gln Val Glu Ile Leu Ser Asn Gly Lys Tyr Lys Ser Val
        275             280             285

Tyr His Arg Thr Thr Val Asn Lys Asp Lys Thr Arg Met Ser Trp Pro
    290             295             300

Val Phe Leu Glu Pro Pro Ser Glu His Glu Val Gly Pro Ile Pro Lys
305             310             315             320

Leu Leu Ser Glu Ala Asn Pro Pro Lys Phe Lys Thr Lys Lys Tyr Lys
                325             330             335

Asp Tyr Val Tyr Cys Lys Leu Asn Lys Leu Pro
            340             345

( 2 ) INFORMATION FOR SEQ ID NO:3:

( i ) SEQUENCE CHARACTERISTICS:
        ( A ) LENGTH: 890 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 3..725

( x i ) SEQUENCE DESCRIPTION: SEQ ID NO:3:

```
GC GTA CCA CAA GAA GAG AAA GAG ATG ATT GCA AAG AGT CCA GGG TCG        47
   Val Pro Gln Glu Glu Lys Glu Met Ile Ala Lys Ser Pro Gly Ser
       350                 355                 360

CAG AAT ATT GAA GGG TAT GGT ACA TCT TTG CAG AAG GAA GTT GAA GGG       95
Gln Asn Ile Glu Gly Tyr Gly Thr Ser Leu Gln Lys Glu Val Glu Gly
            365                 370                 375

AAA AGA GGT TGG GTT GAT CAT TTG TTT CAT AAG ATT TGG CCT CCT TCT      143
Lys Arg Gly Trp Val Asp His Leu Phe His Lys Ile Trp Pro Pro Ser
380                 385                 390

GCC ATC AAT TAT CGT TAT TGG CCT AAA AAC CCT CCT TCC TAC AGG GAA      191
Ala Ile Asn Tyr Arg Tyr Trp Pro Lys Asn Pro Pro Ser Tyr Arg Glu
395                 400                 405                 410

GCA AAT GAG GAA TAT GCA AAG AGG CTG CGA GAA GTT GCG GAG AAG ATG      239
Ala Asn Glu Glu Tyr Ala Lys Arg Leu Arg Glu Val Ala Glu Lys Met
                415                 420                 425

TTT AAG AGC TTA TCA CTT GGG CTT GGG TTA GAA GCC CAT GAA ATG ATG      287
Phe Lys Ser Leu Ser Leu Gly Leu Gly Leu Glu Ala His Glu Met Met
            430                 435                 440
```

```
GAG  GCA  GCA  GGT  GGT  GAA  GAT  ATA  GTT  TAC  TTG  TTG  AAG  ATC  AAT  TAT    335
Glu  Ala  Ala  Gly  Gly  Glu  Asp  Ile  Val  Tyr  Leu  Leu  Lys  Ile  Asn  Tyr
          445                     450                     455

TAC  CCA  CCA  TGC  CCA  AGG  CCT  GAT  TTG  GCA  CTT  GGA  GTT  GTG  GCC  CAT    383
Tyr  Pro  Pro  Cys  Pro  Arg  Pro  Asp  Leu  Ala  Leu  Gly  Val  Val  Ala  His
     460                     465                     470

ACA  GAC  ATG  TCC  CAT  ATA  ACC  ATT  CTT  GTC  CCA  AAT  GAA  GTC  CAA  GGC    431
Thr  Asp  Met  Ser  His  Ile  Thr  Ile  Leu  Val  Pro  Asn  Glu  Val  Gln  Gly
475                     480                     485                     490

CTC  CAA  GTC  TTC  AAG  GAT  GGC  CAT  TGG  TAT  GAT  GTC  AAC  TAC  ATA  CCA    479
Leu  Gln  Val  Phe  Lys  Asp  Gly  His  Trp  Tyr  Asp  Val  Asn  Tyr  Ile  Pro
               495                     500                     505

AAT  GCC  CTA  ATT  GTC  CAC  ATT  GGT  GAC  CAA  CTT  GAG  ATC  CTT  AGC  AAT    527
Asn  Ala  Leu  Ile  Val  His  Ile  Gly  Asp  Gln  Leu  Glu  Ile  Leu  Ser  Asn
               510                     515                     520

GGG  AAA  TAC  AAG  AGT  GTG  TAT  CAT  AGG  ACA  ACA  GTG  ACA  AAG  GAT  AAG    575
Gly  Lys  Tyr  Lys  Ser  Val  Tyr  His  Arg  Thr  Thr  Val  Thr  Lys  Asp  Lys
               525                     530                     535

ACA  AGA  ATG  TCA  TGG  CCA  GTT  TTC  TTG  GAG  CCA  CCA  TCA  GAG  CAT  GAA    623
Thr  Arg  Met  Ser  Trp  Pro  Val  Phe  Leu  Glu  Pro  Pro  Ser  Glu  His  Glu
     540                     545                     550

GTT  GGG  CCA  ATT  CCT  AAG  CTG  GTT  AAT  GAG  GCC  AAT  CCA  CCC  AAA  TTC    671
Val  Gly  Pro  Ile  Pro  Lys  Leu  Val  Asn  Glu  Ala  Asn  Pro  Pro  Lys  Phe
555                     560                     565                     570

AAG  ACC  AAG  AAG  TAC  AAG  GAT  TAT  GTC  TAT  TGT  AAG  CTT  AAC  AAG  CTT    719
Lys  Thr  Lys  Lys  Tyr  Lys  Asp  Tyr  Val  Tyr  Cys  Lys  Leu  Asn  Lys  Leu
                    575                     580                     585

CCT  CAG  TGAAGAAACT  CCTCTATATA  TGTTTGGCAG  CGATTAGCTA  CTATATGTTC            775
Pro  Gln

GTCAGTATTA  TATTATGGTT  TGTACTATCC  TTACCAACAG  ATGTCTTATT  ATGATTAAGG           835

ACTATATATT  TACACTTAAA  ACTTTTGAT  ACTAGCTAAT  AACTGACTTA  TTAAG                890
```

( 2 ) INFORMATION FOR SEQ ID NO:4:

( i ) SEQUENCE CHARACTERISTICS:
        ( A ) LENGTH: 241 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Val  Pro  Gln  Glu  Glu  Lys  Glu  Met  Ile  Ala  Lys  Ser  Pro  Gly  Ser  Gln
 1                  5                    10                      15

Asn  Ile  Glu  Gly  Tyr  Gly  Thr  Ser  Leu  Gln  Lys  Glu  Val  Glu  Gly  Lys
               20                      25                      30

Arg  Gly  Trp  Val  Asp  His  Leu  Phe  His  Lys  Ile  Trp  Pro  Pro  Ser  Ala
          35                      40                      45

Ile  Asn  Tyr  Arg  Tyr  Trp  Pro  Lys  Asn  Pro  Pro  Ser  Tyr  Arg  Glu  Ala
     50                      55                      60

Asn  Glu  Glu  Tyr  Ala  Lys  Arg  Leu  Arg  Glu  Val  Ala  Glu  Lys  Met  Phe
65                      70                      75                      80

Lys  Ser  Leu  Ser  Leu  Gly  Leu  Gly  Leu  Glu  Ala  His  Glu  Met  Met  Glu
               85                      90                      95

Ala  Ala  Gly  Gly  Glu  Asp  Ile  Val  Tyr  Leu  Leu  Lys  Ile  Asn  Tyr  Tyr
              100                     105                     110

Pro  Pro  Cys  Pro  Arg  Pro  Asp  Leu  Ala  Leu  Gly  Val  Val  Ala  His  Thr
              115                     120                     125
```

| Asp | Met | Ser | His | Ile | Thr | Ile | Leu | Val | Pro | Asn | Glu | Val | Gln | Gly | Leu |
|---|---|---|---|---|---|---|---|---|---|---|---|---|---|---|---|
| | 130 | | | | 135 | | | | | 140 | | | | | |

| Gln | Val | Phe | Lys | Asp | Gly | His | Trp | Tyr | Asp | Val | Asn | Tyr | Ile | Pro | Asn |
|---|---|---|---|---|---|---|---|---|---|---|---|---|---|---|---|
| 145 | | | | | 150 | | | | | 155 | | | | | 160 |

| Ala | Leu | Ile | Val | His | Ile | Gly | Asp | Gln | Leu | Glu | Ile | Leu | Ser | Asn | Gly |
|---|---|---|---|---|---|---|---|---|---|---|---|---|---|---|---|
| | | | | 165 | | | | | 170 | | | | | 175 | |

| Lys | Tyr | Lys | Ser | Val | Tyr | His | Arg | Thr | Thr | Val | Thr | Lys | Asp | Lys | Thr |
|---|---|---|---|---|---|---|---|---|---|---|---|---|---|---|---|
| | | | 180 | | | | | 185 | | | | | 190 | | |

| Arg | Met | Ser | Trp | Pro | Val | Phe | Leu | Glu | Pro | Pro | Ser | Glu | His | Glu | Val |
|---|---|---|---|---|---|---|---|---|---|---|---|---|---|---|---|
| | | 195 | | | | | 200 | | | | | 205 | | | |

| Gly | Pro | Ile | Pro | Lys | Leu | Val | Asn | Glu | Ala | Asn | Pro | Pro | Lys | Phe | Lys |
|---|---|---|---|---|---|---|---|---|---|---|---|---|---|---|---|
| | 210 | | | | | 215 | | | | | 220 | | | | |

| Thr | Lys | Lys | Tyr | Lys | Asp | Tyr | Val | Tyr | Cys | Lys | Leu | Asn | Lys | Leu | Pro |
|---|---|---|---|---|---|---|---|---|---|---|---|---|---|---|---|
| 225 | | | | | 230 | | | | | 235 | | | | | 240 |

Gln ( 2 ) INFORMATION FOR SEQ ID NO:5:

( i ) SEQUENCE CHARACTERISTICS:
        ( A ) LENGTH: 236 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 1..135

( x i ) SEQUENCE DESCRIPTION: SEQ ID NO:5:

| CCA | GTA | TTC | TTG | GAG | CCA | CCA | TCA | GAG | CAT | GAA | GTA | GGG | CCA | ATT | TCT | 48 |
|---|---|---|---|---|---|---|---|---|---|---|---|---|---|---|---|---|
| Pro | Val | Phe | Leu | Glu | Pro | Pro | Ser | Glu | His | Glu | Val | Gly | Pro | Ile | Ser | |
| | | | | 245 | | | | 250 | | | | | 255 | | | |

| AAG | CTG | GTT | AAT | GAG | GCC | AAT | CCA | CCC | AAA | TTC | AAG | ACC | AAG | AAG | TAC | 96 |
|---|---|---|---|---|---|---|---|---|---|---|---|---|---|---|---|---|
| Lys | Leu | Val | Asn | Glu | Ala | Asn | Pro | Pro | Lys | Phe | Lys | Thr | Lys | Lys | Tyr | |
| | | 260 | | | | | 265 | | | | | 270 | | | | |

| AAG | GAT | TAT | GTT | TAT | TGT | AAG | CTT | AAC | AAG | CTT | CCT | CAG | TGAAGAAACC | | | 145 |
|---|---|---|---|---|---|---|---|---|---|---|---|---|---|---|---|---|
| Lys | Asp | Tyr | Val | Tyr | Cys | Lys | Leu | Asn | Lys | Leu | Pro | Gln | | | | |
| | 275 | | | | | 280 | | | | | 285 | | | | | |

CCTCTATATA TGTTTGGCAG CGAATAGCTA GTATATTCGT GAGTACTAAA TTATGGTTTG     205

TACTATCCTT ACCAAGAGAT GTCTTATTAT G     236

( 2 ) INFORMATION FOR SEQ ID NO:6:

( i ) SEQUENCE CHARACTERISTICS:
        ( A ) LENGTH: 45 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Pro | Val | Phe | Leu | Glu | Pro | Pro | Ser | Glu | His | Glu | Val | Gly | Pro | Ile | Ser |
|---|---|---|---|---|---|---|---|---|---|---|---|---|---|---|---|
| 1 | | | | 5 | | | | | 10 | | | | | 15 | |

| Lys | Leu | Val | Asn | Glu | Ala | Asn | Pro | Pro | Lys | Phe | Lys | Thr | Lys | Lys | Tyr |
|---|---|---|---|---|---|---|---|---|---|---|---|---|---|---|---|
| | | | 20 | | | | | 25 | | | | | 30 | | |

| Lys | Asp | Tyr | Val | Tyr | Cys | Lys | Leu | Asn | Lys | Leu | Pro | Gln |
|---|---|---|---|---|---|---|---|---|---|---|---|---|
| | | 35 | | | | | 40 | | | | | 45 |

( 2 ) INFORMATION FOR SEQ ID NO:7:

( i ) SEQUENCE CHARACTERISTICS:
        ( A ) LENGTH: 1236 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 70..1068

( x i ) SEQUENCE DESCRIPTION: SEQ ID NO:7:

```
GAATTCGGCA  CGAGGTTAAA  TCAAAAATAT  AAAACAAACA  AATAAATAAA  TAAATAAATA            60

AATAAAAGT  ATG  GGC  ATA  TCT  TCA  GAA  AGA  GTA  CAA  AAC  ATA  GCC  TTA       108
           Met  Gly  Ile  Ser  Ser  Glu  Arg  Val  Gln  Asn  Ile  Ala  Leu
                 50                             55

AAA  TCC  CAG  AAC  ATA  GAC  GAC  ATT  CCA  CCC  GAA  TAC  ATA  AGA  TTA  GAG    156
Lys  Ser  Gln  Asn  Ile  Asp  Asp  Ile  Pro  Pro  Glu  Tyr  Ile  Arg  Leu  Glu
      60                     65                          70

GAT  GAA  CAA  CCA  GCA  ATC  ACA  ACA  GTC  CTC  GAC  ACG  GTT  CTC  GAG  GTC    204
Asp  Glu  Gln  Pro  Ala  Ile  Thr  Thr  Val  Leu  Asp  Thr  Val  Leu  Glu  Val
 75                      80                        85                        90

CCT  GCG  ATC  GAC  CTC  AGC  CTC  GAG  GAA  GAC  GAC  GTT  GTA  AAA  CTC  GTC    252
Pro  Ala  Ile  Asp  Leu  Ser  Leu  Glu  Glu  Asp  Asp  Val  Val  Lys  Leu  Val
                      95                        100                   105

TTG  AGT  GCA  AGC  AAA  GAG  TGG  GGA  CTG  TTT  CAG  GTC  ACC  AAC  CAC  GGA    300
Leu  Ser  Ala  Ser  Lys  Glu  Trp  Gly  Leu  Phe  Gln  Val  Thr  Asn  His  Gly
                110                       115                      120

ATT  CCG  ACT  GAA  GTC  ATT  GAA  AAA  TTG  CAA  AAA  GTC  GGT  AAG  ATG  TTT    348
Ile  Pro  Thr  Glu  Val  Ile  Glu  Lys  Leu  Gln  Lys  Val  Gly  Lys  Met  Phe
           125                      130                     135

TTT  CGA  GCT  CCC  GCA  GAG  GAG  AAG  GAG  ACG  ATT  GCG  AAA  CCC  GAG  GGT    396
Phe  Arg  Ala  Pro  Ala  Glu  Glu  Lys  Glu  Thr  Ile  Ala  Lys  Pro  Glu  Gly
      140                     145                     150

GGT  GTT  GAA  GGG  TAT  GGG  ACC  ATG  TTG  CAA  AAG  GAG  ATT  CAA  GGG  AGA    444
Gly  Val  Glu  Gly  Tyr  Gly  Thr  Met  Leu  Gln  Lys  Glu  Ile  Gln  Gly  Arg
155                      160                     165                      170

AAA  GGT  TGG  GTT  GAT  CAT  TTG  TTT  CAC  AAG  GTT  TGG  CCT  CCT  AGT  GTT    492
Lys  Gly  Trp  Val  Asp  His  Leu  Phe  His  Lys  Val  Trp  Pro  Pro  Ser  Val
                      175                     180                      185

ATT  AAC  TAC  CAA  TGG  TGG  CCT  AAG  ACT  CCT  TCT  TAT  AGG  GAG  GCG  AAC    540
Ile  Asn  Tyr  Gln  Trp  Trp  Pro  Lys  Thr  Pro  Ser  Tyr  Arg  Glu  Ala  Asn
                190                      195                     200

GAA  GAG  TAC  ACA  AAG  TAC  CTA  AGA  ATA  GTA  GCC  GAC  AAG  CTC  TTC  AAG    588
Glu  Glu  Tyr  Thr  Lys  Tyr  Leu  Arg  Ile  Val  Ala  Asp  Lys  Leu  Phe  Lys
           205                     210                     215

TGT  ATG  TCA  AAG  GGA  CTT  GGT  TTA  GAA  GAA  GAT  GAA  GTC  AAA  AAA  TCA    636
Cys  Met  Ser  Lys  Gly  Leu  Gly  Leu  Glu  Glu  Asp  Glu  Val  Lys  Lys  Ser
      220                     225                     230

TGT  GGC  AAT  GAA  GAC  ATA  GTG  TAC  CTT  CTC  AAG  ATC  AAC  TAC  TAC  CCG    684
Cys  Gly  Asn  Glu  Asp  Ile  Val  Tyr  Leu  Leu  Lys  Ile  Asn  Tyr  Tyr  Pro
235                      240                     245                      250

CCT  TGT  CCT  CGA  CCC  GAC  TTG  GCT  CTA  GGG  GTG  GCC  GCT  CAC  ACT  GAC    732
Pro  Cys  Pro  Arg  Pro  Asp  Leu  Ala  Leu  Gly  Val  Ala  Ala  His  Thr  Asp
                      255                     260                      265

TTG  AGC  GTC  ATC  ACC  ATT  CTT  GTT  CCG  AAT  GAT  GTT  GCC  GGT  CTT  CAG    780
Leu  Ser  Val  Ile  Thr  Ile  Leu  Val  Pro  Asn  Asp  Val  Ala  Gly  Leu  Gln
                270                      275                     280
```

```
GTC  TCT  AGA  GAC  GGA  CGT  TGG  TAC  GAT  GTC  AAG  TAC  ATT  CCT  AAT  GCA        828
Val  Ser  Arg  Asp  Gly  Arg  Trp  Tyr  Asp  Val  Lys  Tyr  Ile  Pro  Asn  Ala
          285                 290                      295

CTC  ATC  ATC  CAC  GTT  GGT  GAC  CAA  ATG  GAG  ATA  ATG  AGC  AAT  GGA  GAG        876
Leu  Ile  Ile  His  Val  Gly  Asp  Gln  Met  Glu  Ile  Met  Ser  Asn  Gly  Glu
     300                      305                      310

TAC  AAG  GCG  GTG  CTT  CAT  AGG  TCG  ACA  GTG  AAC  AAA  GAA  AGA  ACA  AGG        924
Tyr  Lys  Ala  Val  Leu  His  Arg  Ser  Thr  Val  Asn  Lys  Glu  Arg  Thr  Arg
315                      320                      325                      330

ATA  TCG  TGG  CCC  GTG  TTC  CTG  GAA  CCG  CCA  TCA  GAC  TTT  GCA  GTC  GGG        972
Ile  Ser  Trp  Pro  Val  Phe  Leu  Glu  Pro  Pro  Ser  Asp  Phe  Ala  Val  Gly
               335                      340                      345

CCT  ATT  CCA  AAG  CTC  ATT  AGT  GAT  GAA  AAG  CCA  GCC  AAG  TAT  AAG  ACG       1020
Pro  Ile  Pro  Lys  Leu  Ile  Ser  Asp  Glu  Lys  Pro  Ala  Lys  Tyr  Lys  Thr
               350                      355                      360

AAG  GTG  TTT  TCC  GAG  TAC  AAG  TAT  TGT  AAG  CTG  AAC  AAG  CTA  CCT  ATG       1068
Lys  Val  Phe  Ser  Glu  Tyr  Lys  Tyr  Cys  Lys  Leu  Asn  Lys  Leu  Pro  Met
          365                      370                      375

TGAAGACTGA  AGATGTTTAA  TATTAGTCTT  ATATGTTTAA  TAAAGGCTAT  TGTTGGTTAT            1128

CAGTTATCAC  CTTGTTATTT  GAATGTGCCA  CTAAAATCAC  TGTTAATTAA  GGTGATATGG            1188

ATATATGATT  TGTTCTCATT  CATGTATGTT  AAAAAAAAAA  AAAAAAA                          1236
```

( 2 ) INFORMATION FOR SEQ ID NO:8:

( i ) SEQUENCE CHARACTERISTICS:
        ( A ) LENGTH: 333 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met  Gly  Ile  Ser  Ser  Glu  Arg  Val  Gln  Asn  Ile  Ala  Leu  Lys  Ser  Gln
 1             5                      10                           15

Asn  Ile  Asp  Asp  Ile  Pro  Pro  Glu  Tyr  Ile  Arg  Leu  Glu  Asp  Glu  Gln
               20                  25                      30

Pro  Ala  Ile  Thr  Thr  Val  Leu  Asp  Thr  Val  Leu  Glu  Val  Pro  Ala  Ile
               35                       40                      45

Asp  Leu  Ser  Leu  Glu  Glu  Asp  Asp  Val  Val  Lys  Leu  Val  Leu  Ser  Ala
      50                       55                       60

Ser  Lys  Glu  Trp  Gly  Leu  Phe  Gln  Val  Thr  Asn  His  Gly  Ile  Pro  Thr
 65                       70                       75                       80

Glu  Val  Ile  Glu  Lys  Leu  Gln  Lys  Val  Gly  Lys  Met  Phe  Phe  Arg  Ala
                    85                       90                       95

Pro  Ala  Glu  Glu  Lys  Glu  Thr  Ile  Ala  Lys  Pro  Glu  Gly  Gly  Val  Glu
               100                      105                      110

Gly  Tyr  Gly  Thr  Met  Leu  Gln  Lys  Glu  Ile  Gln  Gly  Arg  Lys  Gly  Trp
               115                      120                      125

Val  Asp  His  Leu  Phe  His  Lys  Val  Trp  Pro  Pro  Ser  Val  Ile  Asn  Tyr
     130                      135                      140

Gln  Trp  Trp  Pro  Lys  Thr  Pro  Ser  Tyr  Arg  Glu  Ala  Asn  Glu  Glu  Tyr
145                      150                      155                      160

Thr  Lys  Tyr  Leu  Arg  Ile  Val  Ala  Asp  Lys  Leu  Phe  Lys  Cys  Met  Ser
                    165                      170                      175

Lys  Gly  Leu  Gly  Leu  Glu  Glu  Asp  Glu  Val  Lys  Lys  Ser  Cys  Gly  Asn
               180                      185                      190

Glu  Asp  Ile  Val  Tyr  Leu  Leu  Lys  Ile  Asn  Tyr  Tyr  Pro  Pro  Cys  Pro
               195                      200                      205
```

```
Arg  Pro  Asp  Leu  Ala  Leu  Gly  Val  Ala  Ala  His  Thr  Asp  Leu  Ser  Val
     210                           215                      220

Ile  Thr  Ile  Leu  Val  Pro  Asn  Asp  Val  Ala  Gly  Leu  Gln  Val  Ser  Arg
225                      230                      235                      240

Asp  Gly  Arg  Trp  Tyr  Asp  Val  Lys  Tyr  Ile  Pro  Asn  Ala  Leu  Ile  Ile
                    245                      250                      255

His  Val  Gly  Asp  Gln  Met  Glu  Ile  Met  Ser  Asn  Gly  Glu  Tyr  Lys  Ala
               260                      265                      270

Val  Leu  His  Arg  Ser  Thr  Val  Asn  Lys  Glu  Arg  Thr  Arg  Ile  Ser  Trp
          275                      280                      285

Pro  Val  Phe  Leu  Glu  Pro  Pro  Ser  Asp  Phe  Ala  Val  Gly  Pro  Ile  Pro
     290                      295                      300

Lys  Leu  Ile  Ser  Asp  Glu  Lys  Pro  Ala  Lys  Tyr  Lys  Thr  Lys  Val  Phe
305                      310                      315                      320

Ser  Glu  Tyr  Lys  Tyr  Cys  Lys  Leu  Asn  Lys  Leu  Pro  Met
                    325                      330
```

(2) INFORMATION FOR SEQ ID NO:9:

(i) SEQUENCE CHARACTERISTICS:
        (A) LENGTH: 1250 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 11..1015

(xi) SEQUENCE DESCRIPTION: SEQ ID NO:9:

```
AGCACACACA  ATG  GAG  GTG  GAA  AGA  GTT  CAA  GAA  ATA  GCA  ACA  CTC  TCA                49
            Met  Glu  Val  Glu  Arg  Val  Gln  Glu  Ile  Ala  Thr  Leu  Ser
            335                      340                      345

AAC  CTA  AAT  GGC  ACA  ATC  CCA  AGT  GAG  TTC  ATA  AGA  CTG  GAA  AAC  GAA          97
Asn  Leu  Asn  Gly  Thr  Ile  Pro  Ser  Glu  Phe  Ile  Arg  Leu  Glu  Asn  Glu
               350                      355                      360

CAA  CCA  GCA  ACG  ACC  ACT  CTC  CAT  GGC  GTC  TTG  TTG  GAG  GTT  CCA  GTG         145
Gln  Pro  Ala  Thr  Thr  Thr  Leu  His  Gly  Val  Leu  Leu  Glu  Val  Pro  Val
          365                      370                      375

ATC  GAT  CTT  AGC  CAG  GCG  GAT  AAC  GAA  TCC  TTG  GTC  GCT  TTG  ATA  TCC         193
Ile  Asp  Leu  Ser  Gln  Ala  Asp  Asn  Glu  Ser  Leu  Val  Ala  Leu  Ile  Ser
     380                      385                      390

AAA  GCG  AGC  AAG  GAT  TGG  GGT  ATT  TTT  CAA  GTG  GTG  AAC  CAT  GGG  ATA         241
Lys  Ala  Ser  Lys  Asp  Trp  Gly  Ile  Phe  Gln  Val  Val  Asn  His  Gly  Ile
395                      400                      405                      410

CCA  AGT  GAA  CTC  ATT  AGC  AAG  TTA  CAA  AAT  GTT  GGA  AAA  GAG  TTC  TTT         289
Pro  Ser  Glu  Leu  Ile  Ser  Lys  Leu  Gln  Asn  Val  Gly  Lys  Glu  Phe  Phe
                    415                      420                      425

GAG  CTA  CCA  CAA  GAA  GAA  AAA  GAA  GTC  ATT  GCT  AAA  CCA  GAT  GGT  TAC         337
Glu  Leu  Pro  Gln  Glu  Glu  Lys  Glu  Val  Ile  Ala  Lys  Pro  Asp  Gly  Tyr
               430                      435                      440

AAA  GGT  GTT  GAA  GGG  TAT  GGA  ACA  AAG  CTT  CAA  AAA  GAA  GTT  CAA  GGC         385
Lys  Gly  Val  Glu  Gly  Tyr  Gly  Thr  Lys  Leu  Gln  Lys  Glu  Val  Gln  Gly
          445                      450                      455

AAG  AAA  GGA  TGG  GTG  GAT  CAT  TTG  TTT  CAT  ATA  GTT  TGG  CCA  CCT  TCT         433
Lys  Lys  Gly  Trp  Val  Asp  His  Leu  Phe  His  Ile  Val  Trp  Pro  Pro  Ser
     460                      465                      470
```

| | | | | | | | | | | | | | | | | |
|---|---|---|---|---|---|---|---|---|---|---|---|---|---|---|---|---|
| TTT | ATT | AAC | TAT | CAA | TTT | TGG | CCA | AAG | AAC | CCT | CCT | TCT | TAC | AGA | GAT | 481 |
| Phe | Ile | Asn | Tyr | Gln | Phe | Trp | Pro | Lys | Asn | Pro | Pro | Ser | Tyr | Arg | Asp | |
| 475 | | | | 480 | | | | | 485 | | | | | | 490 | |
| ACA | AAT | GAG | GAA | TAC | ACA | CAA | AGC | TTG | ATA | GGG | GTG | GCA | AAT | AAG | TTG | 529 |
| Thr | Asn | Glu | Glu | Tyr | Thr | Gln | Ser | Leu | Ile | Gly | Val | Ala | Asn | Lys | Leu | |
| | | | | 495 | | | | | 500 | | | | | 505 | | |
| CTT | GGG | CTG | TTG | TCA | AAA | GGG | CTT | GGA | CTG | GAA | GAA | GAT | GAA | GTG | AAG | 577 |
| Leu | Gly | Leu | Leu | Ser | Lys | Gly | Leu | Gly | Leu | Glu | Glu | Asp | Glu | Val | Lys | |
| | | | 510 | | | | | 515 | | | | | 520 | | | |
| CAA | GCG | TTG | GGT | GGC | GAA | GAC | TTG | ATC | TAC | ATG | TTG | AAA | ATA | AAC | TAC | 625 |
| Gln | Ala | Leu | Gly | Gly | Glu | Asp | Leu | Ile | Tyr | Met | Leu | Lys | Ile | Asn | Tyr | |
| | | 525 | | | | | 530 | | | | | 535 | | | | |
| TAC | CCA | CCA | TGT | CCA | TGC | CCC | GAG | CTT | GCT | CTT | GGG | GTA | GCC | CCA | CAT | 673 |
| Tyr | Pro | Pro | Cys | Pro | Cys | Pro | Glu | Leu | Ala | Leu | Gly | Val | Ala | Pro | His | |
| | 540 | | | | 545 | | | | | 550 | | | | | | |
| ACC | GAC | ATG | TCT | TCA | ATC | ACC | ATA | CTT | GTC | CCG | AAT | GAA | GTT | CAA | GGT | 721 |
| Thr | Asp | Met | Ser | Ser | Ile | Thr | Ile | Leu | Val | Pro | Asn | Glu | Val | Gln | Gly | |
| 555 | | | | | 560 | | | | | 565 | | | | | 570 | |
| CTA | CAA | GTC | TTT | AAA | GAT | GGT | CAA | TGG | TAT | GAT | GTT | GCT | TAC | ATT | CCT | 769 |
| Leu | Gln | Val | Phe | Lys | Asp | Gly | Gln | Trp | Tyr | Asp | Val | Ala | Tyr | Ile | Pro | |
| | | | | 575 | | | | | 580 | | | | | 585 | | |
| AAT | GCT | CTC | ATT | ATT | CAC | ATT | GGT | GAC | CAG | ATT | GAG | ATA | CTG | AGC | AAT | 817 |
| Asn | Ala | Leu | Ile | Ile | His | Ile | Gly | Asp | Gln | Ile | Glu | Ile | Leu | Ser | Asn | |
| | | | 590 | | | | | 595 | | | | | 600 | | | |
| GGA | AAA | TAT | AAG | AGT | GTG | TAT | CAC | AGA | TCA | ACT | GTG | AAT | AAG | GAG | AAA | 865 |
| Gly | Lys | Tyr | Lys | Ser | Val | Tyr | His | Arg | Ser | Thr | Val | Asn | Lys | Glu | Lys | |
| | | 605 | | | | | 610 | | | | | 615 | | | | |
| ACA | AGA | ATG | TCG | TGG | CCA | GCA | TTT | TTG | GAG | CCA | CCG | CCA | GAG | TTT | GAG | 913 |
| Thr | Arg | Met | Ser | Trp | Pro | Ala | Phe | Leu | Glu | Pro | Pro | Pro | Glu | Phe | Glu | |
| | 620 | | | | 625 | | | | | 630 | | | | | | |
| GTT | GGT | CCA | ATT | CCA | AAG | CTC | GTC | AAT | AAA | GAC | GAT | CCA | CCA | AAA | TAC | 961 |
| Val | Gly | Pro | Ile | Pro | Lys | Leu | Val | Asn | Lys | Asp | Asp | Pro | Pro | Lys | Tyr | |
| 635 | | | | | 640 | | | | | 645 | | | | | 650 | |
| AAG | ACC | AAG | AAG | TAC | AAA | GAC | TAT | GTC | TAT | TGC | AAG | CTA | AAT | AAG | CTT | 1009 |
| Lys | Thr | Lys | Lys | Tyr | Lys | Asp | Tyr | Val | Tyr | Cys | Lys | Leu | Asn | Lys | Leu | |
| | | | | 655 | | | | | 660 | | | | | 665 | | |

| | | | |
|---|---|---|---|
| CCG | CAG | TGAGGGATTT TAGATATTAT CTGCAAACAT ATATGTATTT CTGAACGCAT | 1065 |
| Pro | Gln | | |

GCGTGTGTAA GCTGTTGAGT TATTTGAATG TGGGATTGTA ATATGAGACT CTGATCGAAT 1125

TTAGTTCAAA GCTATATGAA CATACAATAA GAGGAGTAAC TCATTCATCC ACTTTGGCAT 1185

TTTCATCCTT TATATTCGAT ATTAGGTATG TATCATGCTT TACAAGGTAA AAAAAAAAA 1245

AAAAA 1250

( 2 ) INFORMATION FOR SEQ ID NO:10:

( i ) SEQUENCE CHARACTERISTICS:
  ( A ) LENGTH: 335 amino acids
  ( B ) TYPE: amino acid
  ( D ) TOPOLOGY: linear ( i i ) MOLECULE TYPE: protein ( x i ) SEQUENCE DESCRIPTION: SEQ ID NO:10:

| | | | | | | | | | | | | | | | |
|---|---|---|---|---|---|---|---|---|---|---|---|---|---|---|---|
| Met | Glu | Val | Glu | Arg | Val | Gln | Glu | Ile | Ala | Thr | Leu | Ser | Asn | Leu | Asn |
| 1 | | | | 5 | | | | | 10 | | | | | 15 | |
| Gly | Thr | Ile | Pro | Ser | Glu | Phe | Ile | Arg | Leu | Glu | Asn | Glu | Gln | Pro | Ala |
| | | | 20 | | | | | 25 | | | | | 30 | | |
| Thr | Thr | Thr | Leu | His | Gly | Val | Leu | Leu | Glu | Val | Pro | Val | Ile | Asp | Leu |
| | | 35 | | | | | 40 | | | | | 45 | | | |

| | | | | | | | | | | | | | | |
|---|---|---|---|---|---|---|---|---|---|---|---|---|---|---|
| Ser | Gln | Ala | Asp | Asn | Glu | Ser | Leu | Val | Ala | Leu | Ile | Ser | Lys | Ala | Ser |
| | 50 | | | | | 55 | | | | 60 | | | | |
| Lys | Asp | Trp | Gly | Ile | Phe | Gln | Val | Val | Asn | His | Gly | Ile | Pro | Ser | Glu |
| 65 | | | | 70 | | | | | 75 | | | | | 80 |
| Leu | Ile | Ser | Lys | Leu | Gln | Asn | Val | Gly | Lys | Glu | Phe | Phe | Glu | Leu | Pro |
| | | | | 85 | | | | | 90 | | | | | 95 |
| Gln | Glu | Glu | Lys | Glu | Val | Ile | Ala | Lys | Pro | Asp | Gly | Tyr | Lys | Gly | Val |
| | | | 100 | | | | | 105 | | | | | 110 | | |
| Glu | Gly | Tyr | Gly | Thr | Lys | Leu | Gln | Lys | Glu | Val | Gln | Gly | Lys | Lys | Gly |
| | | | 115 | | | | | 120 | | | | | 125 | | |
| Trp | Val | Asp | His | Leu | Phe | His | Ile | Val | Trp | Pro | Pro | Ser | Phe | Ile | Asn |
| | | 130 | | | | 135 | | | | | 140 | | | | |
| Tyr | Gln | Phe | Trp | Pro | Lys | Asn | Pro | Pro | Ser | Tyr | Arg | Asp | Thr | Asn | Glu |
| 145 | | | | | 150 | | | | | 155 | | | | | 160 |
| Glu | Tyr | Thr | Gln | Ser | Leu | Ile | Gly | Val | Ala | Asn | Lys | Leu | Leu | Gly | Leu |
| | | | | 165 | | | | | 170 | | | | | 175 | |
| Leu | Ser | Lys | Gly | Leu | Gly | Leu | Glu | Glu | Asp | Glu | Val | Lys | Gln | Ala | Leu |
| | | | 180 | | | | | 185 | | | | | 190 | | |
| Gly | Gly | Glu | Asp | Leu | Ile | Tyr | Met | Leu | Lys | Ile | Asn | Tyr | Tyr | Pro | Pro |
| | | 195 | | | | | 200 | | | | | 205 | | | |
| Cys | Pro | Cys | Pro | Glu | Leu | Ala | Leu | Gly | Val | Ala | Pro | His | Thr | Asp | Met |
| | 210 | | | | | 215 | | | | | 220 | | | | |
| Ser | Ser | Ile | Thr | Ile | Leu | Val | Pro | Asn | Glu | Val | Gln | Gly | Leu | Gln | Val |
| 225 | | | | | 230 | | | | | 235 | | | | | 240 |
| Phe | Lys | Asp | Gly | Gln | Trp | Tyr | Asp | Val | Ala | Tyr | Ile | Pro | Asn | Ala | Leu |
| | | | | 245 | | | | | 250 | | | | | 255 | |
| Ile | Ile | His | Ile | Gly | Asp | Gln | Ile | Glu | Ile | Leu | Ser | Asn | Gly | Lys | Tyr |
| | | | 260 | | | | | 265 | | | | | 270 | | |
| Lys | Ser | Val | Tyr | His | Arg | Ser | Thr | Val | Asn | Lys | Glu | Lys | Thr | Arg | Met |
| | | | 275 | | | | | 280 | | | | | 285 | | |
| Ser | Trp | Pro | Ala | Phe | Leu | Glu | Pro | Pro | Pro | Glu | Phe | Glu | Val | Gly | Pro |
| | | 290 | | | | | 295 | | | | | 300 | | | |
| Ile | Pro | Lys | Leu | Val | Asn | Lys | Asp | Asp | Pro | Pro | Lys | Tyr | Lys | Thr | Lys |
| 305 | | | | | 310 | | | | | 315 | | | | | 320 |
| Lys | Tyr | Lys | Asp | Tyr | Val | Tyr | Cys | Lys | Leu | Asn | Lys | Leu | Pro | Gln | |
| | | | | 325 | | | | | 330 | | | | | 335 | |

( 2 ) INFORMATION FOR SEQ ID NO:11:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

GAGAGAGAGA GAGAGAGAGA TCTCGAGTTT TTTTTTTTT TTTTT    45

( 2 ) INFORMATION FOR SEQ ID NO:12:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
    ( D ) OTHER INFORMATION: (X,Y) =either X or Y
        N =inosine ( x i ) SEQUENCE DESCRIPTION: SEQ ID NO:12:

TGGGGNNTTT TYSANNTNRT NRANCA                                                26

( 2 ) INFORMATION FOR SEQ ID NO:13:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( D ) OTHER INFORMATION: (X,Y) =either X or Y
            N =inosine ( x i ) SEQUENCE DESCRIPTION: SEQ ID NO:13:

TNRTNAAYCA YGGNWTNCC                                                        19

( 2 ) INFORMATION FOR SEQ ID NO:14:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( D ) OTHER INFORMATION: (X,Y) =either X or Y
            N =inosine ( x i ) SEQUENCE DESCRIPTION: SEQ ID NO:14:

GGNYTNTTYS ARNTNRTNAA YCAYGG                                                26

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( D ) OTHER INFORMATION: (X,Y) =either X or Y
            N =inosine ( x i ) SEQUENCE DESCRIPTION: SEQ ID NO:15:

GGYTTNGGRC ANGGNGGRTA                                                       20

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( D ) OTHER INFORMATION: (X,Y) =either X or Y
            N =inosine ( x i ) SEQUENCE DESCRIPTION: SEQ ID NO:16:

GGRCANGGNG GRTARTARTT  20

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

GGACAAGGAG GATAATAATT  20

( 2 ) INFORMATION FOR SEQ ID NO:18:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

ATCAGAGTAC ATTAGGTC  18

( 2 ) INFORMATION FOR SEQ ID NO:19:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

GTCCCAAATG AAGTCCAAG  19

( 2 ) INFORMATION FOR SEQ ID NO:20:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

TTCTTCGTTT GCTTCCCT  18

( 2 ) INFORMATION FOR SEQ ID NO:21:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

CTAGGTACCG GGCCCAAAGG ATCCTCTAGA GTAC  34

GENETIC SEQUENCES ENCODING FLAVONOL SYNTHASE ENZYMES AND USES THEREFOR

FIELD OF THE INVENTION

The present invention relates generally to genetic sequences encoding flavonoid metabolising enzymes and in particular enzymes having flavonol synthase activity and their use such as in manipulating production of pigmentory molecules in plants.

BACKGROUND OF THE INVENTION

Bibliographic details of the publications referred to hereinafter in the specification are collected at the end of the description. SEQ ID No's referred to herein in relation to nucleotide and amino acid sequences are defined after the Bibliography.

The flower industry strives to develop new and different varieties of flowering plants. An effective way to create such novel varieties is through the manipulation of flower colour and classical breeding techniques have been used with some success to produce a wide range of colours for most of the commercial varieties of flowers. This approach has been limited, however, by the constraints of a particular species' gene pool and for this reason it is rare for a single species to have a full spectrum of coloured varieties. For example, the development of blue varieties of the major cut flower species such as rose, chrysanthemum, carnation, lily, tulip and gerbera would offer a significant opportunity in both the cut flower and ornamental markets.

The colours of flowers and other plant parts are predominantly due to two types of pigments: flavonoids and carotenoids. Flavonoids are the most common and the most important of the flower pigments. The most important classes of flavonoids with respect to flower colour are anthocyanins, flavonols and flavones. Anthocyanins are glycosylated derivatives of cyanidin, delphinidin, petunidin, peonidin, malvidin and pelargonidin, and are localised in the vacuole.

One important factor for flower colour is co-pigmentation of arithocyanins with tannins and certain flavone and flavonol glycosides (Scott-Moncrieff, 1936). When compared over a range of pH values, co-pigmented anthocyanins are always found to be bluer than the normal pigment. Co-pigmentation of anthocyanins with flavonol glycosides can also be important for the development of colour in fruit (Yoshitama et al., 1992). The molar ratio of anthocyanin to co-pigment can also exert a strong influence on colour. It has recently been demonstrated that flavonol aglycones are essential for pollen germination and pollen tube growth (Mo et al., 1992). The ability to control the production of co-pigments, such as flavonols, in plants could therefore have useful applications in altering flower colour and manipulating plant fertility.

The biosynthetic pathway for the anthocyanin pigments is well established (Ebel and Hahlbrock, 1988; Hahlbrock and Grisebach, 1979; Wiering and de Vlaming, 1984; Schram et al., 1984; Stafford, 1990). The first committed step in the pathway involves the condensation of three molecules of malonyl-CoA with one molecule of p-coumaroyl-CoA. This reaction is catalysed by the enzyme chalcone synthase. The product of this reaction, 2', 4, 4', 6'-tetrahydroxychalcone, is normally rapidly isomerised to produce naringenin by the enzyme chalcone-flavanone isomerase. Naringenin is subsequently hydroxylated at the 3 position of the central ring by flavanone 3-hydroxylase to produce dihydrokaempferol (DHK). The B-ring of dihydrokaempferol can be hydroxylated at either the 3', or both the 3' and 5' positions, to produce dihydroquercetin (DHQ) and dihydromyricetin (DHM), respectively. DHK, DHQ and DHM may be converted to coloured anthocyanins (pelargonidin 3-glucoside, cyanidin 3-glucoside and delphinidin 3-glucoside) by the action of at least two enzymes (dihydroflavonol-4-reductase and flavonoid-3-glucosyltransferase).

Flavonols such as kaempferol (K), quercetin (Q) and myricetin (M) are formed from dihydroflavonols by the introduction of a double bond between C-2 and C-3 (Forkmann, 1991), as illustrated in FIG. 1. Flavonols often accumulate in glycosylated forms and may also be methylated. Methylation can occur either before or after glycosylation. In vitro conversion of dihydroflavonols to flavonols was first observed in enzyme preparations from parsley cell cultures (Britsch er al., 1981). Flavonol synthase activity has also been detected in flower extracts from Matthiola (Spribille and Forkmann, 1984), Petunia (Forkmann et al., 1986) and Dianthus (Forkmann, 1991). Flavonol synthase enzyme activity requires 2-oxoglutarate, ascorbate and ferrous ions as cofactors. In flowers of *Petunia hybrida*, the genetic locus Fl controls the formation of flavonols: flavonol synthesis is greatly reduced in mutants homozygous recessive for this gene (Wiering et al., 1979; Forkmann et al., 1986). In vitro enzyme assays with the flavonol synthase from petunia showed that DHK and DHQ were readily converted to the respective flavonols, whereas DHM was a poor substrate. The ability to control flavonol synthase activity in flowering plants would provide a means to manipulate petal colour by altering flavonol production, thereby enabling a single species to express a broader spectrum of flower colours. As stated above, the ability to control flavonol production also has implications in respect of male fertility. Such control may be by modulating the level of production of an indigenous enzyme or by introducing a non-indigenous enzyme.

SUMMARY OF THE INVENTION

As used herein an "indigenous" enzyme is one which is native to or naturally expressed in a particular cell. A "non-indigenous" enzyme is an enzyme: not native to the cell but expressed through the introduction of genetic material into a plant cell; for example, through a transgene. An "endogenous" enzyme is an enzyme produced by a cell but which may or may not be indigenous to that cell.

In accordance with the present invention, the genetic sequences encoding flavonol synthase (hereinafter referred to as "FLS") have been identified and cloned from a number of sources and used to generate transgenic plants. These recombinant sequences permit the modulation of levels of flavonol production thereby providing a means to manipulate petal colour and male fertility. The recombinant sequences also permit the modulation of DHK metabolism as well as the metabolism of other substrates, such as DHQ and DHM. Since DHK, DHQ and DHM are precursors of the coloured anthocyanins modulation of their concentrations by expression of FLS sequences provides another means of manipulating flower colour.

Accordingly, one aspect of the present invention provides an isolated nucleic acid molecule comprising a sequence of nucleotides encoding, or complementary to a sequence encoding a plant FLS or a functional mutant, derivative, part, fragment, homologue or analogue of said FLS. The expression "FLS" includes reference to polypeptides and proteins having FLS activity as well as any mutants, derivatives, parts, fragments, homologues or analogues of such polypeptides or proteins and which have FLS activity. A molecule having FLS activity may also be a fusion polypeptide or protein between a polypeptide or protein having FLS activity and an extraneous peptide, polypeptide or protein.

As used herein, the term "isolated nucleic acid molecule" is meant to include a genetic sequence in a non-naturally-occurring condition. Generally, this means isolated away from its natural state or formed by procedures not necessarily encountered in its natural environment. More specifically, it includes nucleic acid molecules formed or maintained in vitro, including genomic DNA fragments, recombinant or synthetic molecules and nucleic acids in combination with heterologous nucleic acids such as heterologous nucleic acids fused or operably-linked to the genetic sequences of the present invention. The term "isolated nucleic acid molecule" also extends to the genomic DNA or cDNA, or part thereof encoding FLS or a functional mutant, derivative, part, fragment, homologue or analogue of FLS, in reverse orientation relative to its or another promoter. It further extends to naturally-occurring sequences following at least a partial purification relative to other nucleic acid sequences. The term "isolated nucleic acid molecule" as used herein is understood to have the same meaning as a "nucleic acid isolate".

The expression "genetic sequences" is used herein in its most general sense and encompasses any contiguous series of nucleotide bases specifying directly, or via a complementary series of bases, a sequence of amino acids comprising a FLS molecule including a polypeptide or protein having FLS activity. Such a sequence of amino acids may constitute a full-length FLS such as is set forth in, for example, SEQ ID No:1 or SEQ ID No:4 or SEQ ID No:5 or an active truncated form thereof or a functional mutant, derivative, part, fragment, homologue or analogue thereof. Alternatively, the amino acid sequence may comprise pall of, for example, these sequences or all or part of the sequences set forth in SEQ ID No:2 or SEQ ID No:3.

Another aspect of the present invention provides an isolated nucleic acid molecule comprising a sequence of nucleotides which:

(i) encodes a FLS; and
(ii) has at least 50% nucleotide sequence similarity to the nucleotide sequence set forth in at least one of SEQ ID No:1 or SEQ ID No:2 or SEQ ID No:3 or SEQ ID No:4 or SEQ ID No:5.

More particularly, the present invention is directed to an isolated DNA molecule comprising a sequence of nucleotides which:

(i) encodes a FLS; and
(ii) has at least 65–75% nucleotide sequence similarity to the nucleotide sequence set forth in at least one of SEQ ID No:1 or SEQ ID No:2 or SEQ ID No:3 or SEQ ID No:4 or SEQ ID No:5.

Preferred percentage similarities include 80%, 85%, 90%, 92–95%, 96–98% and 99–100%. Although the percentage similarities referred to above assume an overall comparison between the sequences set forth in at least one of SEQ ID No: 1 or SEQ ID No:2 or SEQ ID No:3 or SEQ ID No:4 or SEQ ID No:5 and another genetic sequence, it is clear that there may be specific regions within the molecules being compared having less than 50% similarity. In this respect, the present invention is further defined as a nucleic acid molecule, and in particular a DNA molecule, comprising a sequence of nucleotides which:

(i) encodes a FLS; and
(ii) has at least 50–75% nucleotide sequence similarity to one or more regions of the sequence set forth in at least one of SEQ ID No:1 or SEQ ID No:2 or SEQ ID No:3 or SEQ ID No:4 or SEQ ID No:5.

The nucleic acid sequences contemplated herein also encompass oligonucleotides useful as genetic probes or as "antisense" molecules capable of regulating expression of the corresponding gene in a plant An "antisense molecule" as used herein may also encompass a gene construct comprising the structural genomic or cDNA gene or part thereof in reverse orientation relative to its or another promoter.

DETAILED DESCRIPTION OF THE INVENTION

With respect to this aspect of the invention there is provided an oligonucleotide of 5–50 nucleotides having substantial similarity or complementary to a part or region of a molecule with a nucleotide sequence set forth in at least one of SEQ ID No:1 or SEQ ID No:2 or SEQ ID No:3 or SEQ ID No:4 or SEQ ID No:5. By "substantial similarity or complementarity" in this context is meant a hybridizable similarity under low, alternatively and preferably medium and alternatively and most preferably high stringency conditions, as defined below. Such an oligonucleotide is useful, for example, in screening FLS genetic sequences from various sources or for monitoring an introduced genetic sequence in a transgenic plant. Such an oligonucleotide is generally in the form of a primer or a probe. Preferably, the oligonucleotide is directed to a conserved FLS genetic sequence or a sequence conserved within a plant genus, plant species and/or plant strain or variety.

In one aspect of the present invention, the oligonucleotide corresponds to the 5' or the 3' end of the FLS genetic sequence. For convenience, the 5' end is considered herein to define a region substantially between the start codon of the structural gene to a centre portion of the gene, and the 3' end is considered herein to define a region substantially between the centre portion of the gene and the terminating codon of the structural gene. It is clear, therefore, that oligonucleotides may hybridize to the 5' end or the 3' end or to a region common to both the 5' and the 3' ends. The present invention extends to all such oligonucleotides.

In one embodiment, the nucleic acid sequence encoding a FLS or a functional mutant, derivative, part, fragment, homologue or analogue thereof is used to reduce the activity of an indigenous FLS, such as by using co-suppression (U.S. Pat. No. 5,034,323). Alternatively, the nucleic acid sequence encoding this enzyme or various functional mutants, derivatives, parts, fragments, homologues or analogues thereof, is used in the antisense orientation to reduce activity of the indigenous FLS. Although not wishing to limit the present invention to any one theory, it is possible that an antisense FLS transcript or fragment or part thereof (for example, an oligonucleotide molecule) would form a duplex with all or part of the naturally-occurring mRNA specified for the enzyme thus preventing accumulation of or translation from the mRNA into active enzyme.

In another alternative, ribozymes could be used to inactivate target nucleic acid sequences. Ribozymes are well described by Haseloff and Gerlach (1988). With respect to this embodiment, the ribozyme would preferably comprise a hybridizing portion and a catalytic portion wherein the hybridizing portion comprises one and preferably two nucleotide arms capable of hybridizing to a mRNA transcript from a gene having a nucleotide sequence substantially as set forth in at least one of SEQ ID No:1 or SEQ ID No:2 or SEQ ID No:3 or SEQ ID No:4 or SEQ ID No:5.

In a further embodiment, the nucleic acid sequence encoding a FLS or a functional mutant, derivative, part, fragment, homologue or analogue thereof is used to elevate the activity of an indigenous FLS above the normal endogenous or existing level, or alternatively to provide FLS activity where the normal endogenous or existing level of activity is negligible or zero.

Reference herein to the altering of FLS activity relates to an elevation or reduction in activity of 30% or more, or more preferably of 30–50%, or even more preferably 50–75% or still more preferably 75% or greater above or below the normal endogenous or existing levels of activity. Such elevation or reduction may be referred to as "modulation" of FLS enzyme activity. Generally, modulation is at the level of transcription or translation of FLS genetic sequences. The level of activity can be assayed using a modified method of Forkmann et al. (1986).

The nucleic acids of the present invention may be ribonucleic ac ids or deoxyribonucleic acids, single stranded or covalently closed circular molecules. Preferably, the nucleic acid molecule is, or originates from, cDNA. The present invention also extends to other nucleic acid molecules which hybridize to the genetic sequences herein disclosed.

According to this aspect of the present invention there is provided an isolated nucleic acid molecule comprising a sequence of nucleotides which:

(i) encodes a FLS; and (ii) hybridizes to the nucleotide sequence set forth in at least one of SEQ ID No:1 or SEQ ID No:2 or SEQ ID No:3 or SEQ ID No:4 or SEQ ID No:5 or a complementary respective form thereof under low stringency conditions.

For the purpose of defining the level of stringency, reference can conveniently be made to Maniatis et al. (1982) at pages 387–389, and especially paragraph 11, which is herein incorporated by reference. A low stringency is defined herein as being in 4–6×SSC/1% (w/v) SDS at 37°–45° C. for 2–3 hours. Depending on the source and concentration of nucleic acid involved in the hybridization, alternative conditions of stringency may be employed such as medium stringent conditions which are considered herein to be 1–4×SSC/0.5–1% (w/v) SDS at greater than or equal to 45° C. for 2–3 hours or high stringent conditions considered herein to be 0.1–1×SSC/0.1–1.0% (w/v) SDS at greater than or equal to 60° C. for 1–3 hours.

In its most preferred embodiment, the present invention extends to a nucleic acid molecule having or comprising a nucleotide sequence set forth in at least one of SEQ ID No:1 or SEQ ID No:2 or SEQ ID No:3 or SEQ ID No:4 or SEQ ID No:5 or to a molecule having at least 50%, more preferably at least 55%, even more preferably at least 60%, still more preferably at least 65–70%, and yet even snore preferably greater than 85% similarity at the level of nucleotide or amino acid sequence to at least one or more regions of the nucleotide or amino acid sequence set forth, respectively, in the above-referenced sequences and wherein the nucleic acid encodes or is complementary to a sequence which encodes an enzyme having FLS activity. It should be noted, however, that nucleotide or amino acid sequences may have similarities below the above given percentages and yet still encode a FLS-like molecule and such molecules may still be considered within the scope of the present invention where they have regions of sequence conservation.

The nucleic acid molecules contemplated herein may exist, in either orientation, alone or in combination with a vector molecule and preferably an expression-vector. The term "vector molecule" is used in its broadest sense to include any intermediate vehicle for the nucleic acid molecule, capable of facilitating transfer of the nucleic acid into the plant cell and/or facilitating integration into the plant genome. An intermediate vehicle may, for example, be adapted for use in electroporation, microprojectile bombardment, Agrobacterium-mediated transfer or insertion via DNA or RNA viruses. The intermediate vehicle and/or the nucleic acid molecule contained therein may or may not need to be stably integrated into the plant genome. Such vector molecules may also replicate and/or express in prokaryotic cells. Preferably, the vector molecules or parts thereof are capable of integration into the plant genome. The nucleic acid molecule may additionally contain a promoter sequence capable of directing expression of the nucleic acid molecule in a plant cell. The nucleic acid molecule and promoter may also be introduced into the cell by any number of means such as those described above. The vector molecule may also comprise a genetic sequence encoding a ribozyme as herein before defined capable of cleaving a FLS mRNA transcript.

The nucleic acid or its complementary form may encode the full-length enzyme or a derivative thereof. By "derivative" is meant any single or multiple amino acid substitutions, deletions, and/or additions relative to the naturally-occurring enzyme and which retains FLS activity. In this regard, the nucleic acid includes the naturally-occurring nucleotide sequence encoding FLS or may contain single or multiple nucleotide substitutions, deletions and/or additions to said naturally-occurring sequence. The nucleic acid sequences of the present invention or its complementary form may also encode a "part" of a FLS, whether active or inactive, and such a nucleic acid molecule may be useful as an oligonucleotide probe, primer for polymerase chain reactions or in various mutagenic techniques, or for the generation of antisense molecules or ribozyme molecules capable of regulating expression of the corresponding gene in a plant.

Amino acid insertional derivatives of the FLS of the present invention include amino and/or carboxyl terminal fusions as well as intra-sequence insertions of single or multiple amino acids. Insertional amino acid sequence variants are those in which one or more amino acid residues are introduced into a predetermined site in the protein although random insertion is also possible with suitable screening of the resulting product. Deletional variants are characterised by the removal of one or more amino acids from the sequence. Substitutional amino acid variants are those in which at least one residue in the sequence has been removed and a different residue inserted in its place. Typical substitutions are those made in accordance with Table 1, overleaf.

Where FLS is derivatised by amino acid substitution, the amino acids are generally replaced by other amino acids having like properties, such as hydrophobicity, hydrophilicity, electronegativity, bulky side chains and the like. Amino acid substitutions are typically of single residues. Amino acid insertions will usually be in the order of about 1–10 amino acid residues and deletions will range from about 1–20 residues. Preferably, deletions or insertions are made in adjacent pairs, i.e. a deletion of two residues or insertion of two residues.

TABLE 1

Suitable residues for amino acid substitutions

| Original Residue | Exemplary Substitutions |
| --- | --- |
| Ala | Ser |
| Arg | Lys |
| Asn | Gln; His |
| Asp | Glu |
| Cys | Ser |
| Gln | Asn; Glu |
| Glu | Asp |
| Gly | Pro |
| His | Asn; Gln |
| Ile | Leu; Val |
| Leu | Ile; Val |
| Lys | Arg; Gln; Glu |
| Met | Leu; Ile; Val |
| Phe | Met; Leu; Tyr |
| Ser | Thr |
| Thr | Ser |
| Trp | Tyr |
| Tyr | Trp; Phe |
| Val | Ile; Leu; Met |

The amino acid variants referred to above may readily be made using peptide synthetic techniques well known in the art, such as solid phase peptide synthesis (Merrifield, 1964) and the like, or by recombinant DNA manipulations. Techniques for making substitution mutations at predetermined sites in DNA having known or partially known sequence are well known and include, for example, M13 mutagenesis. The manipulation of DNA sequence to produce variant proteins which manifest as substitutional, insertional or deletional variants are conveniently described, for example, in Sambrook et al. (1989).

Other examples of recombinant or synthetic mutants and derivatives of the FLS enzyme of the present invention include single or multiple substitutions, deletions and/or additions of any molecule associated with the enzyme such as carbohydrates, lipids and/or proteins or polypeptides.

The terms "analogues" and "derivatives" also extend to any functional chemical equivalent of FLS and also to any amino acid derivative described above. For convenience, reference to "FLS" herein and in particular hereinafter includes reference to any functional mutant, derivative, part, fragment, homologue or analogue thereof.

The present invention is exemplified using nucleic acid sequences derived from petunia, tobacco, carnation and chrysanthemum, since these represent the most convenient and preferred sources of material to date. However, one skilled in the art will immediately appreciate that similar sequences can be isolated from any number of sources such as other plants. All such nucleic acid sequences encoding directly or indirectly FLS are encompassed by the present invention regardless of their source. Examples of other suitable sources of genes encoding FLS enzymes include, but are not limited to rose, snapdragon, lisianthus, cyclamen, grape and parsley.

In accordance with the present invention, a nucleic acid sequence encoding a FLS may be introduced into and expressed in a transgenic plant in either orientation thereby providing a means to convert DHK and/or other suitable substrates, if synthesised in the plant cell, ultimately into flavonols or derivatives of same or alternatively to inhibit such conversion of metabolites by reducing or eliminating endogenous or existing FLS activity. The production of these flavonols will modify petal colour and may contribute to the production of bluer colours via co-pigmentation with anthocyanins. Expression of the nucleic acid sequence in the plant may be constitutive, inducible or developmental and may also be tissue-specific. The term "expression" is used in its broadest sense to include production of RNA or of both RNA and protein. It also extends to partial expression of a nucleic acid molecule.

According to this aspect of the present invention there is provided a method for producing a transgenic flowering plant capable of synthesizing FLS, said method comprising stably transforming a cell of a suitable plant with a nucleic acid sequence which comprises a sequence of nucleotides encoding said FLS under conditions permitting the eventual expression of said nucleic acid sequence, regenerating a transgenic plant from the cell and growing said transgenic plant for a time and under conditions sufficient to permit the expression of the nucleic acid sequence. The transgenic plant may thereby produce non-indigenous FLS at elevated levels relative to the amount expressed in a comparable non-transgenic plant.

Another aspect of the present invention contemplates a method for producing a transgenic plant with reduced indigenous or existing FLS activity, said method comprising stably transforming a cell of a suitable plant with a nucleic acid molecule which comprises a sequence of nucleotides encoding or complementary to a sequence encoding a FLS activity, regenerating a transgenic plant from the cell and where necessary growing said transgenic plant under conditions sufficient to permit the expression of the nucleic acid.

Yet another aspect of the present invention contemplates a method for producing a genetically modified plant with reduced indigenous or existing FLS activity, said method comprising altering the Fl gene through modification of the indigenous sequences via homologous recombination from an appropriately altered Fl gene or derivative or part thereof introduced into the plant cell and regenerating the genetically modified plant from the cell.

In a preferred embodiment, the present invention contemplates a method for producing a transgenic flowering plant exhibiting altered inflorescence properties, said method comprising stably transforming a cell of a suitable plant with a nucleic acid sequence of the present invention, regenerating a transgenic plant from the cell and growing said transgenic plant for a time and under conditions sufficient to permit the expression of the nucleic acid sequence into a FLS. Alternatively, said method may comprise stably transforming a cell of a suitable plant with a nucleic acid sequence of the present invention or its complementary sequence, regenerating a transgenic plant from the cell and growing said transgenic plant for a time and under conditions sufficient to alter the level of activity of the indigenous or existing FLS. Preferably the altered level would be less than the indigenous or existing level of FLS activity in a comparable non-transgenic plant Without wishing to limit the present invention, one theory of mode of action is that reduction of the indigenous FLS activity requires the expression of the introduced nucleic acid sequence or its complementary sequence. However, expression of the introduced genetic sequence or its complement may not be required to achieve the desired effect: namely, a flowering plant exhibiting altered inflorescence properties.

In a related embodiment, the present invention contemplates a method for producing a flowering plant exhibiting altered inflorescence properties, said method comprising alteration of the Fl gene through modification of the indigenous sequences via homologous recombination from an appropriately altered Fl gene or derivative or part thereof introduced into the plant cell, and regenerating the genetically modified plant from the cell.

Preferably, the altered inflorescence includes the production of white, yellow, pink, violet or blue flowers or other colour shades depending on the genotype and physiological conditions of the recipient plant.

Accordingly, the present invention extends to a method for producing a transgenic plant capable of expressing a recombinant gene encoding a FLS or which carries a nucleic acid sequence which is substantially complementary to all or a part of a mRNA molecule optionally transcribable where required to effect regulation of a FLS, said method comprising stably transforming a cell of a suitable plant with the isolated nucleic acid molecule comprising a sequence of nucleotides encoding, or complementary to a sequence encoding, a FLS, where necessary under conditions permitting the eventual expression of said isolated nucleic acid molecule, and regenerating a transgenic plant from the cell. By "suitable plant" is meant a plant capable of producing DHK, or other substrates of FLS, and possessing the appropriate physiological properties required for the development of the colour desired.

The present invention is exemplified by generation of transgenic petunia and tobacco plants containing introduced FLS genetic sequences. The use of petunia and tobacco plants represents a particularly convenient and useful model for the generation of transgenic plants carrying genetic sequences and the results obtained from such transgenic plants are generally applicable to other plants. One skilled in the art will immediately recognise the variations applicable to this method such as increasing or decreasing the expression of the enzyme naturally present in a target plant. This would lead to differing shades of colours. Other suitable target plants, in addition to petunia and tobacco, include but are not limited to rose, carnation, chrysanthemum, gerbera, lisianthus, lily, iris and pelargonium.

The present invention, therefore, extends to all transgenic plants containing all or part of the nucleic acid sequence of the present invention, or antisense forms thereof and/or any homologues or related forms thereof and in particular those transgenic plants which exhibit altered inflorescence properties. The transgenic plants may contain an introduced nucleic acid molecule comprising a nucleotide sequence encoding or complementary to a sequence encoding a FLS. Generally the nucleic acid would be stably introduced into the plant genome, although the present invention also extends to the introduction of a FLS nucleotide sequence within an autonomously-replicating nucleic acid sequence such as a DNA or RNA virus capable of replicating within the plant cell. The invention also extends to seeds from such transgenic plants. Such seeds, especially if coloured, will be useful, inter alia, as proprietary tags for plants. The invention further extends to fruit and to vegetable plants and leaves of, for example, ornamental plants.

Another aspect of the present invention is directed to recombinant forms of FLS. The recombinant forms of the enzymes will provide a source of material for research to develop, for example, more active enzymes and may be useful in developing in vitro systems for production of flavonols and/or coloured compounds.

Still a further aspect of the present invention contemplates the use of the genetic sequences described herein in the manufacture of a genetic construct capable of expressing a FLS or down-regulating an indigenous FLS enzyme in a plant.

Another aspect of the present invention is directed to a prokaryotic or eukaryotic organism carrying a genetic sequence encoding a FLS extrachromasomally in plasmid form. In one embodiment, the plasmid is pCGP481 in *Escherichia coli*. The microorganism *Escherichia coli* strain DH5α containing the plasmid pCGP481 was deposited with the Australian Government Analytical Laboratories, 1 Suakin Street, Pymble, New South Wales, 2037, Australia on Aug. 5, 1993 under Accession Number N93/33236.

The present invention is further described by reference to the following non-limiting Figures and Examples.

The amino acid abbreviations used throughout the specification, including in the Examples, are shown overleaf in Table 2.

TABLE 2

| Amino acid | 3-letter | single-letter |
|---|---|---|
| L-alanine | Ala | A |
| L-arginine | Arg | R |
| L-asparagine | Asn | N |
| L-aspartic acid | Asp | D |
| L-cysteine | Cys | C |
| L-glutamine | Gln | Q |
| L-glutamic acid | Glu | E |
| L-glycine | Gly | G |
| L-histidine | His | H |
| L-isoleucine | Ile | I |
| L-leucine | Leu | L |
| L-lysine | Lys | K |
| L-methionine | Met | M |
| L-phenylalanine | Phe | F |
| L-proline | Pro | P |
| L-serine | Ser | S |
| L-threonine | Thr | T |
| L-tryptophan | Trp | W |
| L-tyrosine | Tyr | Y |
| L-valine | Val | V |

Table 3 provides a summary of the SEQ ID No's assigned to genetic sequences referred to herein:

TABLE 3

| Sequence | SEQ ID No |
|---|---|
| cDNA insert of pCGP481 | SEQ ID No: 1 |
| cDNA insert of pCGP489 | SEQ ID No:2 |
| cDNA insert of pCGP490 | SEQ ID No:3 |
| cDNA insert of pCGP777 | SEQ ID No:4 |
| cDNA insert of PCGP874 | SEQ ID No:5 |
| Oligo #1 | SEQ ID No:6 |
| Oligo #2 | SEQ ID No:7 |
| Oligo #3 | SEQ ID No:8 |
| Oligo #4 | SEQ ID No:9 |
| Oligo #5 | SEQ ID No:10 |
| Oligo #6 | SEQ ID No:11 |
| Oligo #7 | SEQ ID No:12 |
| Oligo #8 | SEQ ID No:13 |
| Oligo #9 | SEQ ID No:14 |
| Oligo #10 | SEQ ID No:15 |
| Oligo #11 | SEQ ID No:16 |

EXAMPLE 1

MATERIALS

Enzymes

Figure 1:
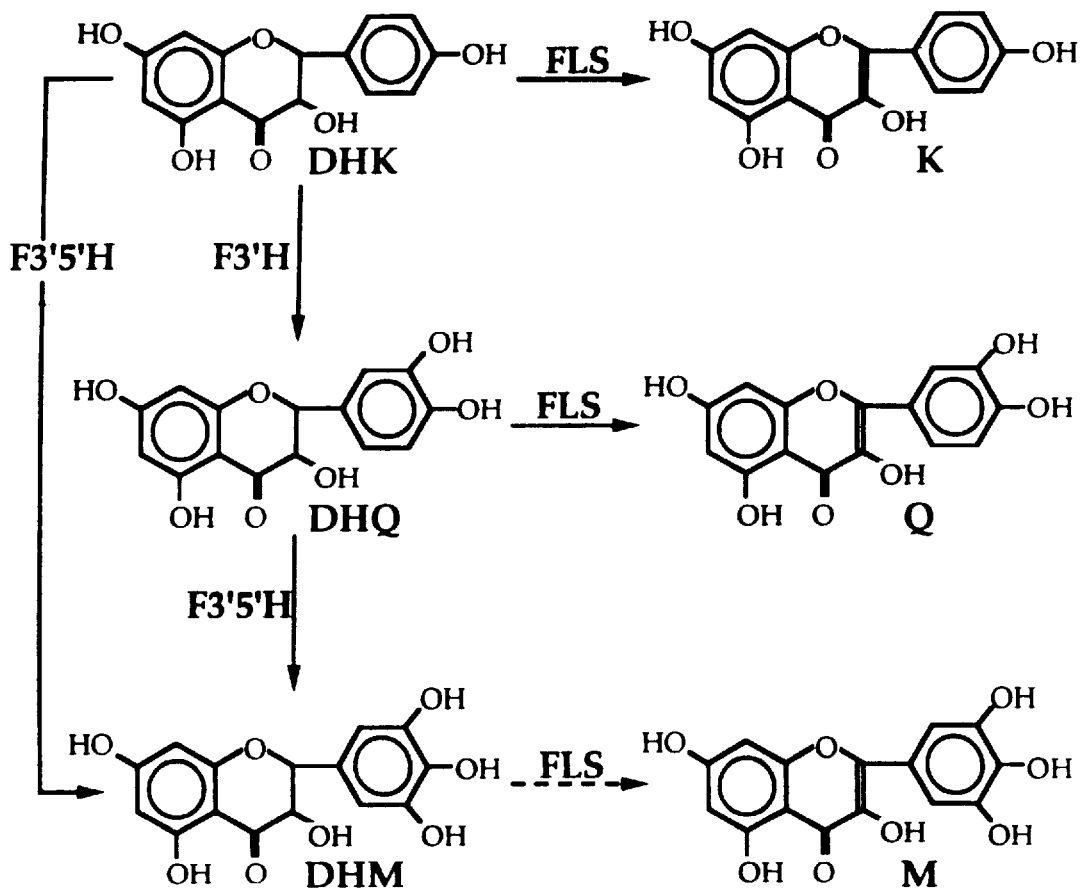
FIG. 1 is a schematic representation of the conversion of dihydroflavonols to flavonols in *Petunia hybrida*. Enzymes involved in each step of the pathway are indicated as follows: F3'H=Flavonoid 3'-hydroxylase; F3'5'H=Flavonoid 3',5'-hydroxylase; FLS=flavonol synthase. DHK= dihydrokaempferol, DHQ=dihydroquercetin, DHM= dihydromyricetin, K=kaempferol, Q=quercetin, M=myricetin.

All enzymes were obtained from commercial sources and used according to the manufacturer's recommendations.

Bacterial Strains

The following *Eschetichia coli* strins were used: PLK-F' and SURE, both obtained from Stratagene; XL1-Blue (Bullock et al,1987), and DH5α (Hanahan, 1983 and BRL, 1986). The *Agrobacterium tumefaciens* strain used was the disarmed AGL0(Lazo et aL, 1991).

Plant Material

The *Petunia hybrida* varieties used are indicated in Table 4, overleaf.

Flowers of *Dianthus caryophyllus* cv. Laguna were obtained from Van Wyk and Son Flower Supply, Victoria.

*Chrysanthemum morifolium* cultivars were obtained from Baguley Flower and Plant Growers, Victoria.

EXAMPLE 2

PLANT GROWING CONDITIONS & STAGES

Growth of plants

*Petunia hybrida* plants were grown in specialised growth rooms with a 14 hour day length at a light intensity of 10,000 lux and a temperature of 22° to 26° C. OGB flowers were harvested at developmental stages defined as follows:

Stage 1: Unpigmented, closed bud (<25 mm in length).

Stage 2: Pigmented, closed bud (25–35 mm in length).

Stage 3: Dark purple bud with emerging corolla (>35 mm in length).

Stage 4: Dark purple opened flower pre-anther dehiscence (>50 mm in length).

Stage 5: Fully opened flower with all anthers dehisced.

TABLE 4

| Plant variety | Genotype | Source/Reference |
| --- | --- | --- |
| Old Glory Blue (F1 Hybrid) | An1, An2, An3, An4, An6, An8, An9, An10, An11, Hf1, Ht1, Rt, Po, Bl, Fl (inferred from phenotype) | Ball Seed, USA |
| V23 | An1, An2, An3, An4, An6 An8, An9, An10, ph1, Hf1, Hf2, ht1, Rt, po, Bl, Fl. | Wallroth et al. 1986 Doodeman et al. 1984 |
| R51 | An1, An2, An3, an4, An6, An8, An9, An10, An11, Ph1, hf1, hf2, Ht1, rt, Po, bl, fl | Wallroth et al. 1986 van Tunen et al. 1990 Doodeman et al. 1984 |
| Ba20 | an1, An2, an4, An6, hf1, hf2, Ht1, Ph1, Ph2, Ph5, Gf, mfl, mf2, Rt, fl | E. Farcy INRA, Dijon |
| V26 | An1, An2, An3, an4, An6, An8, An9, An10, An11, Ht1, Hf1, hf2, Ph1, ph2, Ph5, mfl, mf2, Mt1, Mt2, po, Gf, Rt, Fl | A. Gerats Free University Amsterdam |

Flowers of the other petunia varieties were harvested prior to anther dehiscence, at the stage of maximum pigment accumulation.

Stages of *Dianthus caryophyllus* flower development were defined as follows:

Stage 1: No visible flower bud.

Stage 2: Flower buds opening: tips of florets visible.

Stage 3: Tips of nearly all florets exposed; outer florets opening, none horizontal.

Stage 4: Outer florets horizontal.

Stages of Chrysanthemum flower development were defined as follows:

Stage 0: No visible flower bud.

Stage 1: Flower bud visible: florets completely covered by the bracts.

Stage 2: Flower buds opening: tips of florets visible.

Stage 3: Florets tightly overlapped.

Stage 4: Tips of nearly all florets exposed; outer florets opening but none horizontal.

Stage 5: Outer florets horizontal.

Stage 6: Flower approaching maturity.

EXAMPLE 3

Synthesis of Oligonucleotides

Oligonucleotides were synthesised on an Applied Biosystems PCR-Mate DNA synthesiser using methods recommended by the manufacturer. The oligonucleotides synthesised were, 5'-3':

| Oligo 1: | GAGAGAGAGAGAGAGAGAGATCTCGAGTTTTTTTTTTTTTTTTT | SEQ ID No:6 |
| --- | --- | --- |
| Oligo 2: | TGGGGIITTTT(T,C)(C,G)AIITTI(A,G)TI(A,G)AICA | SEQ ID No:7 |
| Oligo 3: | TI(A,G)TIAA(T,C)CA(T,C)GGI(A,T)TICC | SEQ ID No:8 |
| Oligo 4: | GGI(T,C)TTTT(T,C)(C,G)A(A,G)ITI(A,G)TIAA(T,C)CA(T,C)GG | SEQ ID No:9 |
| Oligo 5: | GG(T,C)TTIGG(A,G)CAIGGIGG(A,G)TA | SEQ ID No:10 |
| Oligo 6: | GG(A,G)CAIGGIGG(A,G)TA(A,G)TA(A,G)TT | SEQ ID No:11 |

-continued

| | | |
|---|---|---|
| Oligo 7: | ATCAGAGTACATTAGGTC | SEQ ID No:12 |
| Oligo 8: | GTCCCAAATGAAGTCCAAG | SEQ ID No:13 |
| Oligo 9: | TTCTTCGTTTGCTTCCCT | SEQ ID No:14 |
| Oligo 10: | CTAGGTACCGGGCCCAAAGGATCCTCTAGAGTAC | SEQ ID No:15 |
| Oligo 11: | TCTAGAGGATCCTTTGGGCCCGGTAC | SEQ ID No:16 |

Where two nucleotides are given in parentheses, this indicates a choice of one or other of the nucleotides; the abbreviation "I" represents deoxyinosine.

EXAMPLE 4

CLONING OF A DIOXYGENASE FROM PETUNIA

Construction of a petunia cDNA library

Total RNA was isolated from the petal tissue of *P. hybrida* cv. OGB stage 3 to 4 flowers using the method of Turpen and Griffith (1986). Poly (A)$^+$RNA was selected from the total RNA by three cycles of oligo-dT cellulose chromatography (Aviv and Leder, 1972).

Two micrograms of poly(A)$^+$RNA were reverse transcribed in a 20 µL volume containing 1×Superscript™ reaction buffer, 10 mM dithiothireitol, 500 µM dATP, 500 µM dGTP, 500 µM dTTP, 500 µM 5-methyl-dCTP, 0.75 µg Oligo 1 (SEQ ID No:6) and 2 µL Superscript™ reverse transcriptase (BRL). The reaction mix was incubated at 37° C. for 50 minutes, 44° C. for 10 minutes, then placed on ice.

Second strand reaction mix (140 µL) was added to the first strand reaction. The second strand reaction mix consisted of 21 mM Tris-HCl, 104 mM KCl, 5.3 mM MgCl$_2$, 171 µM β-NAD, 11.4 mM (NH$_4$)$_2$SO$_4$, 214 µM dATP, 642 µM dCTP, 214 mM dGTP, 214 µM dTTP, 4 mM DTT, 10 µCi $^{32}$P-dCTP (3000 Ci/mmole), 15 units *E. coli* DNA ligase, 40 units *E. coli* DNA polymerase I (Boehringer) and 0.8 units RNAse H. The final mixture was incubated for 150 minutes at 16° C. To make the double-stranded cDNA blunt-ended, 10 units of T4 DNA polymerase was added, and the reaction was continued for a further 15 minutes at 16° C. The reaction was stopped and the cDNA purified by phenol/chloroform extraction, followed by chloroform extraction and ethanol precipitation.

EcoRI adaptors (Promega) were ligated with the cDNA and then kinased with polynucleotide kinase (Amersham) using conditions recommended by the manufacturer. The enzymes were denatured by heat (70° C. for 20 minutes) and the DNA was purified by phenol/chloroform extraction and ethanol precipitation. The cDNA was digested with 50 units XhoI (Boehringer) in a reaction volume of 100 µL, using conditions recommended by the manufacturer. The enzyme was heat killed (70° C. for 20 minutes) and the cDNA digest passed through a Sephacryl S400 spun column (Pharmacia) which had been equilibrated in STE buffer (Sambrook et al., 1989). The eluate was phenol/chloroform extracted and ethanol precipitated. After microcentrifugation at 4° C. for 30 minutes the cDNA pellet was rinsed with 70% (v/v) ethanol, air dried and resuspended in 10 µL of TE buffer (10 mM Tris-HCl, 1 mM EDTA, pH 7.5).

One-quarter of the cDNA (2.5 µL) was ligated with 1 µg of λZAPII EcoRI/XhoI/ CIAP treated vector (Stratagene) in 5 µL reaction buffer consisting of 50 mM Tris-HCl (pH 7.0), 10 mM MgCl$_2$, 10 mM dithiothreitol, 1 mM ATP and 2 units of T4 DNA ligase. The reaction was incubated at 4° C. for 4 days.

After incubating at room temperature for two hours, the ligation reaction mixture was packaged using the Packagene system (Promega). The total number of recombinants was 1×10$^6$. An amount of 1×10$^6$ plaque forming units (pfu) of the packaged cDNA was plated at 50,000 pfu per 15 cm diameter plate after transfecting *E. coli* PLK-F' cells. The plates were incubated at 37° C. for eight hours, then stored overnight at 4° C. Phage were eluted from the plates into phage storage buffer (8 mM MgSO$_4$, 100 mM NaCl, 0.01% (w/v) gelatin, 50 mM Tris-HCl, pH 8.0) to form an amplified cDNA library stock.

Design of dioxygenase oligonucleotide primers

A number of dioxygenases have been sequenced, from organisms as diverse as plants (Matsuda et al., 1991, Martin et al., 1991), fungi and bacteria (Cohen et al., 1990). A characteristic of all these enzymes is the existence of a number of small regions of sequence conservation. Amino acid sequences of a number of different plant dioxygenases were aligned using the CLUSTAL programs of Higgins and Sharp (1988). The sequences used were Candi (Martin et al., 1991), hyoscyamine 6β-hydroxylase (H6H) (Matsuda et al., 1991), flavanone 3-hydroxylase (F3H), E8 (Deikman and Fischer, 1988), A2 (Menssen et al., 1990) and Tom 13 (Holdsworth et al., 1987). This analysis revealed two well-conserved regions, shown in Table 5:

TABLE 5

| | | | |
|---|---|---|---|
| Candi (snapdragon) | WGVMHLINHGVP | — | NYYPKCPQP |
| H6H (*Hyoscyamus niger*) | FGLFQVINHGFP | — | NYYPPCPDP |
| F3H (barley) | WGIFQVIDHGVD | — | NFYPRCPQP |
| E8 (tomato) | WGFFQVNNHGIP | — | NYYPPCPQP |
| A2 (maize) | WGVMHIAGHGIP | — | NYYPRCPQP |
| Tom13 (tomato) | WGFFELVNHGIP | — | SNYPPCPKP |
| Consensus | wGffqvinHGip | | nyYPpCPgP |
| | f  imhlvd  vd | | sf  r  d |
| | v  eiag  f | | n  k  k |

Oligonucleotides were designed to hybridise to genes encoding sequences similar to the consensus sequences. The sequences of each of these oligonucleotides, designated Oligo 2–6 (SEQ ID No's 7–11), are shown above. The inclusion of deoxyinosine (I) covered the different possibilities for codon usage where more than two codons could encode the same amino acid. Deoxyinosine base-pairs with similar efficiency to A, T, G and C (Martin et al., 1985; Ohtsuka et al., 1985).

PCR amplification of petunia dioxygenase gene fragments

Total RNA was isolated from stages 3–4 flowers of Ba20 (flfl) and V26 (FlFl). 25 µg of total RNA was ethanol precipitated, pelleted and resuspended in 10.5 µL water. One µL (0.5 µg) of Oligo 1 (SEQ ID No:6) was added and the mixture was heated at 70° C. for 10 minutes then placed on ice. The following were then added: 4 µL Superscript™ reaction buffer (5×stock), 2 µL of 100 mM dithiothreitol, 0.5 µL of 5 mM dATP, 0.5 µL of 5 mM dCTP, 0.5 µL of 5 mM dGTP, 0.5 µL of 5 mM dTTP, and 0.5 µL of [α-$^{32}$P]-dCTP. The mixture was incubated at 37° C. for 2 minutes. Following the addition of 1 µL (200 units) of Superscript™ reverse transcriptase, the reaction was incubated at 37° C. for 60 minutes and then terminated by the addition of 80 µL of STE. The cDNA was purified by Sephacryl, S200 spun-column chromatography, followed by ethanol precipitation and resuspension in 100 μL TE buffer. This cDNA was used as the template for PCR.

PCR reactions for amplification of petunia dioxygenase gene fragments contained 4 μL of cDNA, 10 mM Tris-HCl (pH 8.3), 50 mM KCl, 2 mM MgCl$_2$, 0.01% (w/v) gelatin, 0.2 mM each dNTP, 0.4 μM each primer and 1.25 units Taq polymerase (Cetus). Reaction mixes (50 μL) were cycled 40 times: 94° C. for 50 seconds; 42° C. for 1 minute; 72° C. for 1 minute. Fifteen microlitres of each PCR vas electrophoresed on a 1.25% (w/v) agarose gel. DNA fragments in the size range 300–500 bp were collected onto NA-45 membrane. The DNA was eluted from the membrane and then ethanol precipitated, pelleted by centrifugation and resuspended in 25 μL of TE buffer. One μL of DNA fragments from each of the V26 PCRs were pooled and $^{32}$P-labelled using an oligo-labelling kit (BRESATEC). DNA fragments from the Ba20 PCRs were labelled in a similar manner.

Isolation of dioxygenase homologues from a petunia petal cDNA library

Duplicate lifts of 16,000 plaques were hybridised with 5×10$^5$ cpm/μL of either the V26 probe or the Ba20 probe, and washed as follows: High stringency conditions (hybridisation: 50% (v/v) formamide, 6×SSC, 1% (w/v) SDS at 42° C. for 16 hours and washing: 2×SSC, 1% (w/v) SDS at 65° C. for 2×15 minutes followed by 0.2×SSC, 1% (w/v) SDS at 65° C. for 2×15 minutes) were used to detect sibling clones. Fourteen clones hybridised to the V26 probe but not the Ba20 probe. A further 12 clones hybridised more strongly to the V26 probe than the Ba20 probe.

Plasmid cDNA clones in pBluescript were rescued from λZAPII clones using the helper phage R408 (Stratagene).

DNA sequencing of this and other clones was performed essentially by the method of Sanger et al. (1977) using the Sequenase enzyme (USB, version 2.1).

EXAMPLE 5

NORTHERN ANALYSIS

Total RNA was isolated from tissue that had been frozen in liquid nitrogen and ground to a fine powder using a mortar and pestle. An extraction buffer of 4M guanidium isothiocyanate, 50 mM Tris-HCl (pH 8.0), 20 mM EDTA, 0.1% (v/v) Sarkosyl, was added to the tissue and the mixture was homogenised for 1 minute using a polytron at maximum speed. The suspension was filtered through Miracloth (Calbiochem) and centrifuged in a JA20 rotor for 10 minutes at 10,000 rpm. The supernatant was collected and made to 0.2 g/mL CsCl (w/v). Samples were then layered over a 10 mL cushion of 5.7M CsCl, 50 mM EDTA (pH 7.0) in 38.5 mL Quick-seal centrifuge tubes (Beckman) and centrifuged at 42,000 rpm for 16 hours at 25° C. in a 70Ti rotor. Pellets were resuspended in TE/SDS (10 mM Tris-HCl (pH 7.5),1 mM EDTA, 0.1% (w/v) SDS) and extracted with phenol:chloroform:isoamyl alcohol (25:24:1) saturated in 10 mM EDTA (pH 7.5). Following ethanol precipitation, the RNA pellets were resuspended in TE/SDS.

Figure 2:
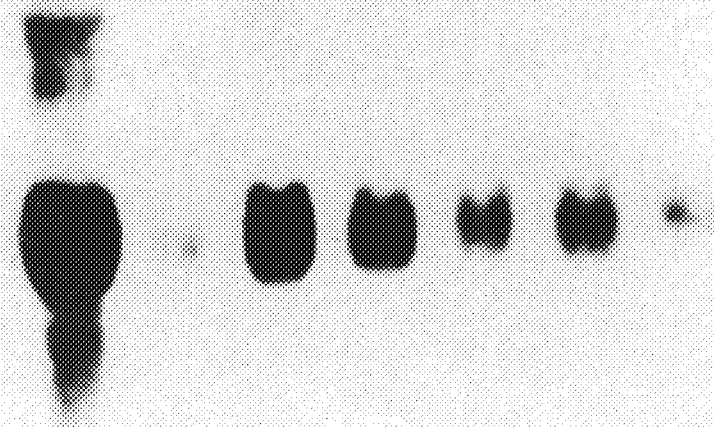
FIG. 2 is an autoradiograph of an RNA gel blot probed with $^{32}$P-labelled pDIOXC3 cDNA insert. Each lane contained 20 μg of total RNA isolated from the following—1–5: OGB limb tissue of flowers at the five stages of development; T: OGB tube tissue from stage 3–4 flowers; L: leaf tissue from six week old OGB seedlings.
Figure 3:
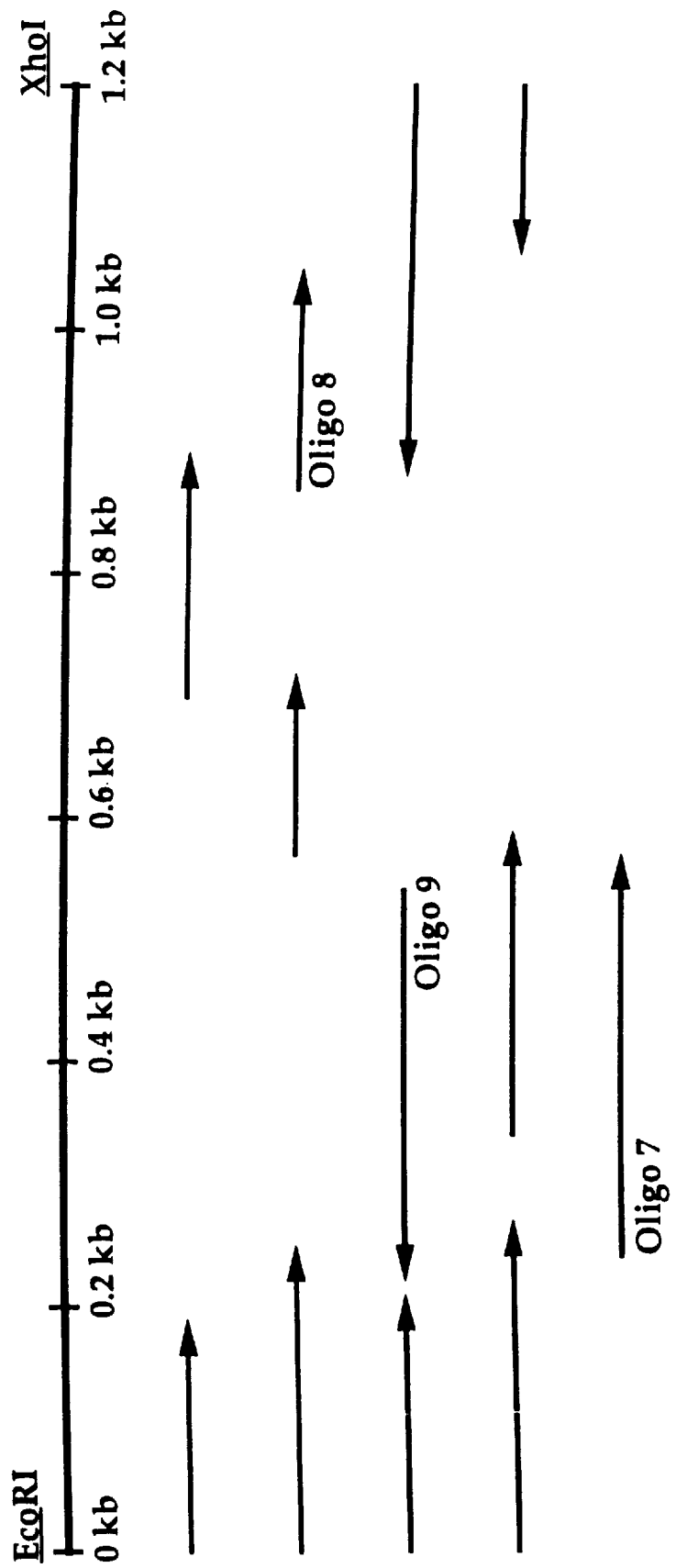
FIG. 3 shows the sequencing strategy used to obtain the complete nucleotide sequence of the cDNA insert of pCGP481. Arrows indicate the direction and length of sequences read from individual sequencing reactions. Sequencing reactions using custom-made oligonucleotide primers (Oligos 7–9; SEQ ID No's 12–14) are also shown.

RNA samples (20 μg) were electrophoresed through a 2.2M formaldehyde/1.2% (w/v) agarose gel using running buffer containing 20 mM morpholinopropanesulphonic acid (pH 7.0), 5 mM sodium acetate, 0.1 mM EDTA (pH 8.0). The RNA was transferred to Hybond-N membrane (Amersham) as recommended by the manufacturer and probed with $^{32}$P-labelled 0.9 kb EcoRI-XhoI pDIOXC3 cDNA fragment (10$^8$ cpm/μg, 2×10$^6$ cpm/μL). Prehybridisation (one hour at 42° C.) and hybridisation (16 hours at 42° C.) were carried out in 50% (v/v) formamide, 1M NaCl, 1% (w/v) SDS, 10% (w/v) dextran sulphate. Degraded salmon sperm DNA (100 μg/mL) was added with the $^{32}$P-labelled probe for the hybridisation step. Filters were washed in 2×SSC/1% (w/v) SDS at 65° C. for 1 to 2 hours and then 0.2×SSC/1% (w/v) SDS at 65° C. for 30 to 60 minutes. Filters were exposed to Kodak XAR film with an intensifying screen at −70° C. for 48 hours (FIG. 2).

RNA gel blot analysis revealed that the gene corresponding to the cDNA clone pDIOXC3 was expressed at the highest level during Stage 1 of flower development and then declined. The expression pattern is similar to that of FLS enzyme activity in petunia flowers (Forkmann et al., 1986).

EXAMPLE 6

RFLP MAPPING OF pDIOXC3

There is one genetic locus in *P. hybrida*, Fl, that controls FLS activity. It was therefore expected that a cDNA clone encoding a *P. hybrida* FLS would map to the Fl locus, provided that the Fl locus encodes the structural gene for FLS. Fl has been mapped to chromosome II of the *P. hybrida* genome and is linked to within 2% recombination of the PAcl gene (Cornu et al., 1990). RFLP analysis of DNA isolated from an F$_2$ population of plants derived from a cross between the inbred lines V23 (FlFl) and R51 (flfl) was used to obtain linkage data for the various dioxygenase homologues.

Isolation of Genomic DNA

DNA was isolated from leaf tissue of V23×R51 F$_2$ plants essentially as described by Dellaporta et al., (1983). The DNA preparations were further purified by CsCl buoyant density centrifugation (Sambrook et al., 1989).

Southern blots

The genomic DNA (10 μg) was digested for 16 hours with 60 units of XbaI and electrophoresed through a 0.7% (w/v) agarose gel in a running buffer of TAE (40 mM Tris-acetate, 50 mM EDTA). The DNA was then denatured in denaturing solution (1.5M NaCl/0.5M NaOH) for 1 to 1.5 hours, neutralised in 0.5M Tris-HCl (pH 7.5)/1.5M NaCl for 2 hours and the DNA was then transferred to a Hybond-N (Amersham) filter in 20×SSC.

DNA fragments (50 to 100 ng) were radioactively labelled with 50 μCi of [α-$^{32}$P]-dCTP using an oligolabelling kit (Bresatec). Unincorporated [α-$^{32}$P]-dCTP was removed by chromatography on a Sephadex G-50 (Fine) column. A PAc1 probe was synthesised from a 2.7 kb HindII/BamHI fragment of pPAcl (Baird and Meagher, 1987). A pDIOXC3 cDNA probe was synthesised from a 0.9 kb EcoRI-XhoI fragment of pDIOXC3.

Duplicate Southern blots of genomic DNA digested with XbaI were hybridised with either the pDIOXC3 probe or the PAc1 probe, to detect RFLP patterns. For 40 out of the 42 plants analysed there was co-segregation of the V23, VR and R51 RFLP patterns for PAc1 with the corresponding RFLP patterns of pDIOXC3, demonstrating the corresponding genes are closely linked (4.7% recombination).

These data provided strong evidence that the gene corresponding to pDIOXC3 is linked to the Fl locus. This linkage, as well as the Northern analysis, provided circumstantial evidence that the pDIOXC3 cDNA might encode FLS.

EXAMPLE 7

ISOLATION OF FULL-LENGTH SIBLING cDNA CLONES OF pDIOXC3

From preliminary sequence analysis it was shown that pDIOXC3 did not represent a full-length clone of the corresponding transcript. To obtain a full-length version of pDIOXC3, approximately 20,000 recombinants from the cDNA library were screened for clones that hybridised to the 0.9 kb EcoRI-XhoI fragment from pDIOXC3. Six clones produced strong hybridisation signals and were chosen for further analysis. A number of clones appeared to be full-length based on agreement between the size of the cDNA insert and the mRNA. The complete sequence of the cDNA insert from one of these clones, designated pCGP481, was determined by compilation of sequence from different pBluescript subclones obtained using standard cloning procedures (Sambrook et al., 1989). For some regions it was necessary to synthesise specific oligonucleotide primers (Oligos 7–9; SEQ ID No's 12–14) to obtain overlapping sequence data. The complete nucleotide sequence and deduced amino acid sequence of pCGP481 is shown as SEQ ID No:1.

EXAMPLE 8

EXPRESSION OF PCGP481 cDNA IN YEAST

Construction of the yeast expression vector pYGA22m M13-mp18 was digested with EcoRI and BglII to produce a 700 bp fragment that contained a multicloning site. This fragment was ligated with the 9 kb EcoRI-BglII fragment from pYGA2269 (Ashikari et al., 1989). The resulting construct, designated pYGA22m, contained the multicloning site inserted downstream of the yeast glyceraldehyde-3-phosphate dehydrogenase promoter.
Construction of pCGP631

Figure 4:
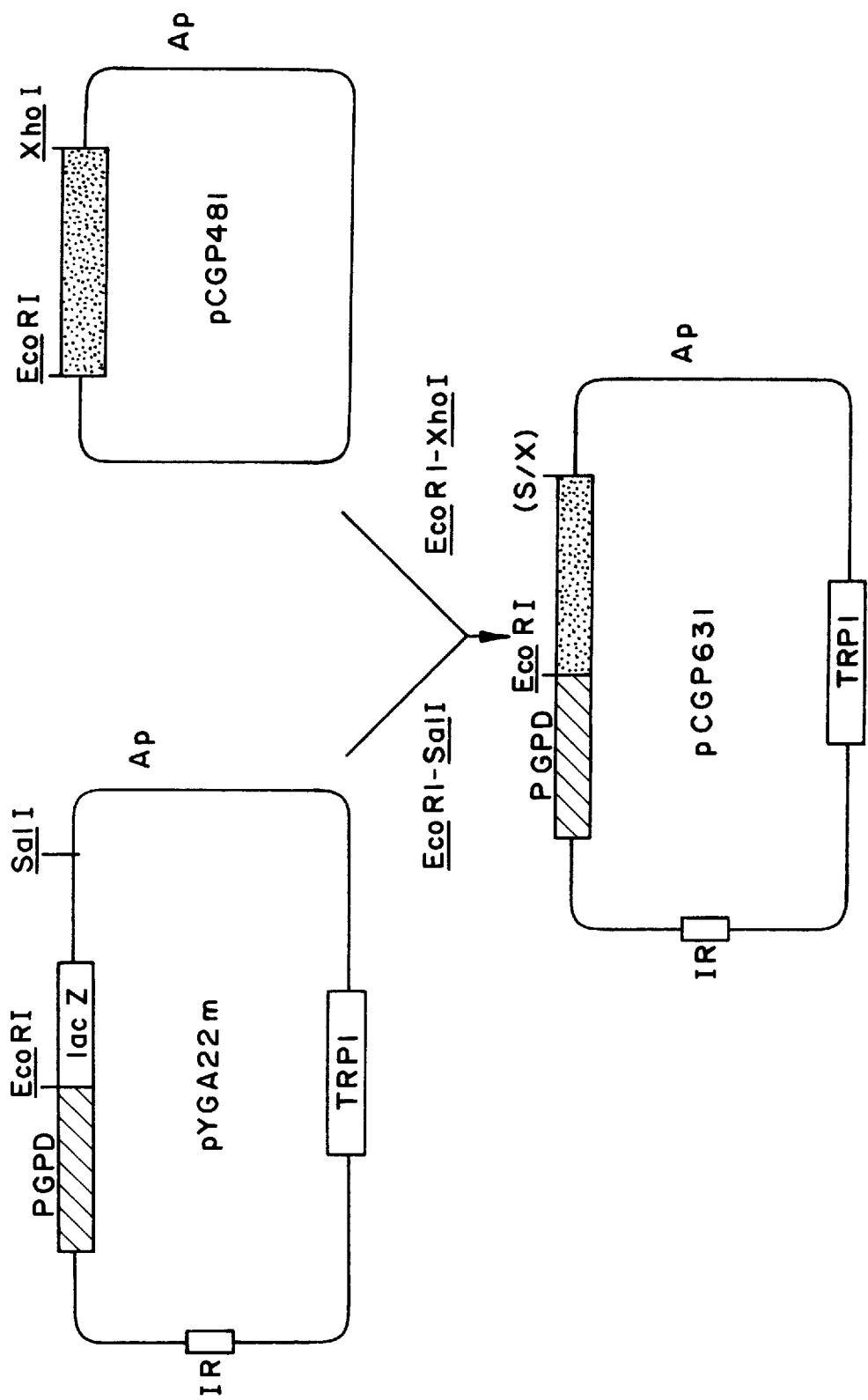
FIG. 4 is a diagrammatic representation of the construction of pCGP631. pCGP631 was constructed by cloning the pCGP481 cDNA insert in a sense orientation behind the yeast glyceraldehyde-3-phosphate dehydrogenase promoter in the expression vector pYGA22m. The cDNA insert from pCGP481 was ligated as a EcoRI/XhoI fragment with the large fragment that resulted from the EcoRI/SalI digestion of pYGA22m. IR=inverted repeat of 2 μm plasmid, TRP1= TRP1 gene, Ap=ampicillin resistance marker.

A 1.3 kb EcoRI-XhoI fragment that included the entire cDNA insert from pCGP481 was ligated with the 9 kb EcoRI/SalI fragment from pYGA22m. The resulting plasmid, designated pCGP631 (FIG. 4), contained the pCGP481 cDNA fragment ligated in a sense orientation behind the glyceraldehyde-3-phosphate dehydrogenase promoter.
Yeast transformation The yeast strain G-1315 (Matα, trpl) (Ashikara et al., 1989) was transformed with pCGP631 according to Ito et al., (1983). The transformants were selected by their ability to restore G-1315 to tryptophan prototrophy.
Preparation of yeast extracts for assay of FLS activity Single isolates of G-1315/pCGP631 and a G-1315 revertant that grew on media lacking tryptophan were used to inoculate 10 mL of YNBC {1.2% (w/v) yeast nitrogen base without amino acids (Difco) and 0.3% (w/v) Casamino acid (Difco)} and incubated with shaking for 2 days at 30° C.

Figure 5:
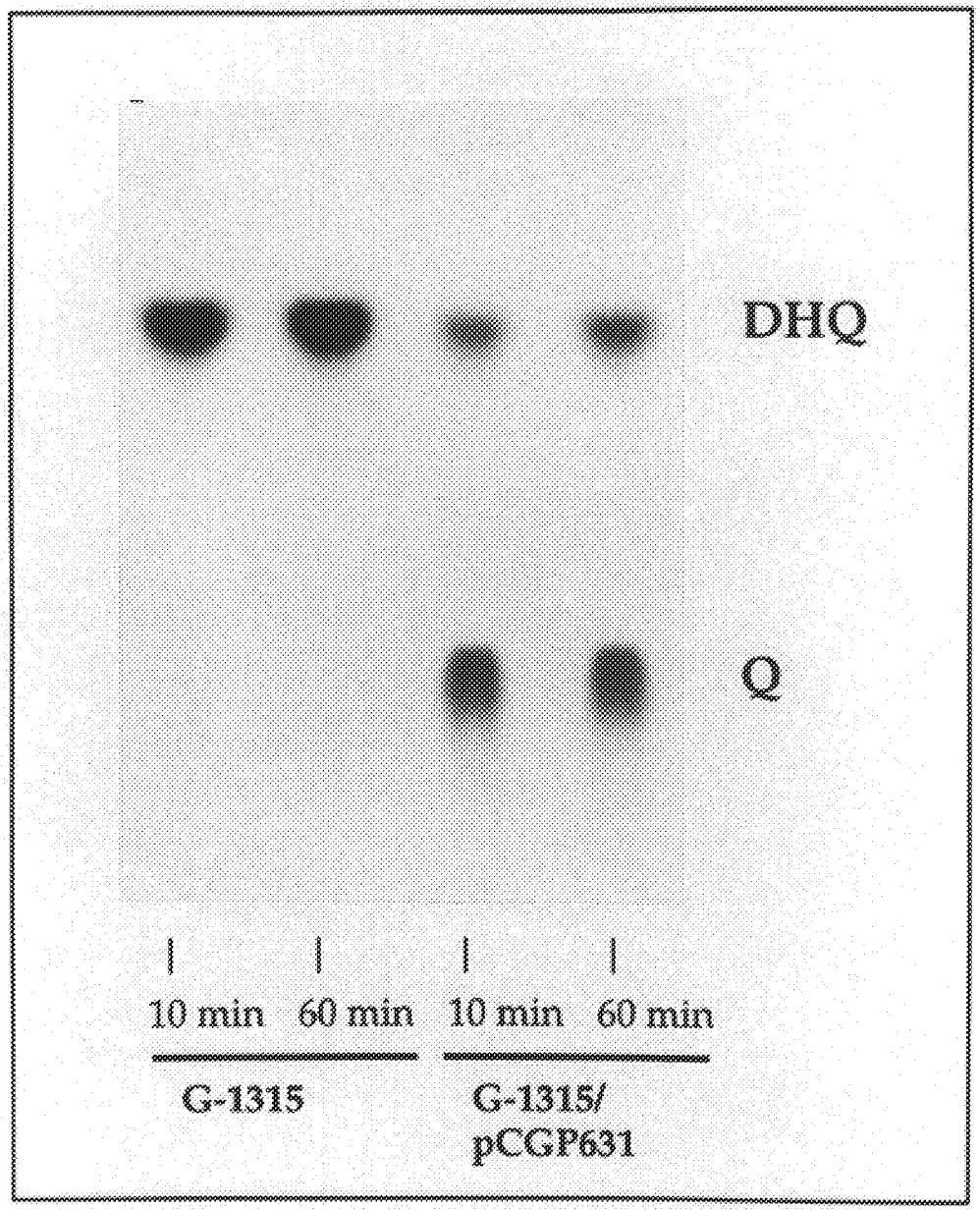
FIG. 5 shows a FLS assay of yeast extracts using DHQ as substrate. The autoradiograph shows conversion of [$^{14}$C]-DHQ to quercetin by enzyme extracts of yeast transformed with the plasmid pCGP631. No FLS activity was detected in untransformed yeast. C=unlabelled quercetin without yeast extract. The position of migration of unlabelled quercetin is circled.

Yeast cells were harvested by centrifugation, washed once with TE buffer and resuspended in 100 μL of buffer B (10 mM Tris-HCl (pH 7.5), 1.2M sorbitol, 0.1 mM DTT, 0.1 mM EDTA) containing zymolyase (0.1 mg/mL) (Seikagakukogyo, Japan) and kept at 30° C. for 1 hour. Spheroplasts were collected by centrifugation and resuspended in 500 μL of 0.1M potassium phosphate buffer (pH 7.0) containing 1 mM 2-mercaptuethanol and 1 mM PMSF. The suspension was then vortexed with glass beads (diameter=0.4 mm) for 2 minutes. The supernatant after centrifugation was used as a crude extract.
FLS assay of yeast enzyme extracts FLS activity was measured by the method of Forkmann et al. (1986) with modifications. The reaction mixture contained in a total of 200 μL: 0.1M potassium phosphate (pH 7.0), 1.4 mM 2-mercaptoethanol, 250 μM 2-oxoglutarate, 5 mM ascorbic acid, 50 μM ferrous sulphate, 5000 cpm of $^{14}$C-DHQ and 40 μL of crude extract. Incubation was carried out for 10 minutes or 1 hour at 30° C. The mixture was immediately extracted with 500 μL of ethyl acetate and chromatographed on a cellulose plate (Merck Art 5577, Germany) with Forestal (acetic acid: HCl: water=30:3:10) along with unlabelled DHQ and quercetin. Radioactivity was localised by autoradiography. An enzyme extract prepared from G-1315/ pCGP631 was shown to have FLS activity while an equivalent fraction prepared from non-transformed yeast had no activity (FIG. 5).

The yeast expression results confirmed that the cDNA insert from pCGP481 encoded an FLS enzyme. Forkmann et al. (1986) suggested that two enzymes, a 2-hydroxylase and a dehydratase, are necessary for the conversion of dihydroflavonols to flavonols. However, the results show that expression the enzyme encoded by the petunia FLS cDNA clone in yeast is sufficient for this conversion, suggesting that only one enzyme is required for the conversion of dihydroflavonols to flavonols.

EXAMPLE 9

MANIPULATION OF FLAVONOL AND ANTHOCYANIN SYNTHESIS IN TRANSGENIC PLANTS

Binary constructs

The binary expression vector pCGP478 was constructed by replacing the XbaI-KpnI fragment of the multiple cloning site from pCGP293 (Brugliera et al., 1993) with a synthetic polylinker containing sites for XbaI, BamHI, ApaI and Asp718. The synthetic polylinker was made by annealing the two oligonucleotides Oligo 10 and Oligo 11 (SEQ ID No's 15 and 16). The order of the restriction enzyme sites between the MAC promoter and the mas terminator of pCGP478 facilitates direct subcloning of cDNA inserts from directional λZAPII clones in an antisense orientation.

A 1.2 kb XbaI/Asp718 fragment containing the complete cDNA from pCGP481 was cloned in an antisense orientation between the MAC promoter and mas terminator of pCGP478 to create pCGP479. The plasmid pCGP479 was introduced into Agrobacterium tumefaciens strain AGL0 (Lazo et al., 1991) using the method of Gynheung et al. (1988). Cells of A. tumefaciens carrying pCGP479 were selected on MG/L agar plates containing 100 μg/mL gentamycin.

A 1.2 kb XbaI/Asp718 fragment containing the cDNA from pCGP481 was cloned in a sense orientation between the MAC promoter and mas terminator of pCGP293 to create pCGP482. The plasmid pCGP482 was introduced into A. tumefaciens strain AGL0 (Lazo et al., 1991) using the method of Gynheung et al. (1988). Cells of A. tumefaciens carrying pCGP482 were selected on MG/L agar plates containing 100 μg/mL gentamycin.
Production of transgenic plants Petunia cv. VR (Flfl) plants were transformed by co-cultivation of leaf discs with AGLO/pCGP479 using the method of Horsch et al. (1985). Transgenic plants were grown to flowering and scored for altered flower colour compared with non-transformed VR flowers. Four out of 12 transgenic plants produced redder flowers than non-transgenic controls. Apart from the change in flower colour in the transgenic petunias no other effects of antisense expression of the FLS cDNA were observed.

Petunia cv. Old Glory Blue plants were transformed by co-cultivation of leaf discs with AGLO/pCGP482 using the method of Horsch et al. (1985). Transgenic plants were grown to flowering and scored for altered flower colour compared with non-transformed Old Glory Blue flowers. Three out of 15 transgenic plants produced redder flowers than non-transgenic controls. Non-transgenic Old Glory Blue flowers are generally blue-violet while the colours of the Old Glory Blue flowers transformed with pCGP482 ranged in colour from blue-violet to purple.

Tobacco plants (*Nicotiana tabacum* cv. Xanthi) were transformed by co-cultivation of leaf discs with AGLO/pCGP479 using the method of Horsch et al. (1985). Tobacco flowers are normally light pink and produce low levels of cyanidin derivatives in the limb of the corolla. Transformation of tobacco with the antisense FLS gene construct caused a reduction in flavonol production and lead to the production of red flowers. Red pigmentation was also increased in the filaments. The red flower colour was due to a three-fold increase in anthocyanin production in the corolla limb.

The colour changes observed may be described in terms of the numbers from the Royal Horticultural Society's Colour Chart as shown in Table 6, overleaf:

TABLE 6

MODIFICATION OF FLOWER COLOUR IN TRANSGENIC PLANTS

| Control: | Petunia cv.VR | Purple-violet | 80A |
|---|---|---|---|
| Transgenic: | VR/pCGP479 | Red-purple | 74A |
| Control: | Petunia cv. Old Glory Blue | Violet-blue | 89A–89C |
| Transgenic: | OGB/pCGP482 | Violet | 83A–83B |
| Control: | *Nicotiana tabacum* cv. Xanthi | Red-purple | 65B |
| Transgenic: | Xanthi/pCGP479 | Red | 51B |

It should be noted, however, that other biochemical and physiological conditions will affect the individual outcome and the citing of the specific colour change achieved by expression of the FLS sense and antisense constructs in transgenic plants should not be interpreted as limiting the possible range of colour changes which may be observed.

Extraction and analysis of flavonoids from flowers

Flavonol aglycones were isolated from petunia flowers by boiling a single corolla in 1 mL of 2M HCl for 30 minutes and extracting the flavonoids with 150 μL ethyl acetate. For thin layer chromatography (TLC), 4 μL of ethyl acetate extracts and 4 μL flavonol standards (kaempferol, quercetin and myricetin) were applied to a TLC plate and developed as described above. Flavonols were visualised under UV light after fuming with ammonia.

Flavonols extracted from petunia VR and petunia VR/pCGP479 flowers were analysed by thin layer chromatography. The red VR/pCGP479 flowers produced markedly less flavonols than non-transgenic VR flowers. Flowers from tobacco plants transformed with pCGP479 were similarly analysed and found to have reduced flavonol content.

Anthocyanins were extracted from petunia and tobacco flowers with 0.5% HCl in methanol. Anthocyanin concentrations were estimated from $A_{530}$ measurements of the extracts as described by Gerats (1985).

EXAMPLE 10

ISOLATION OF cDNA HOMOLOGUES FROM NICOTIANA

Construction and screening of a Nicotiana alata cDNA library

A cDNA library in the vector λZAP was made from RNA isolated from styles of $S_6S_6$ *Nicotiana alata* as described by Chen et al. (1992).

Approximately 36,000 cDNA clones were hybridised with $^{32}$P-labelled pCGP481 cDNA fragment in 6×SSC, 35% (v/v) formamide, 1% (w/v) SDS for 16 hours at 42° C. The filters were washed under medium stringency conditions in 2×SSC, 1% SDS at 65° C. and then autoradiographed. Hybridising plaques were picked off into PSB to allow the phage to elute. Eight plasmid clones were rescued using the single-stranded helper phage VCSM 13 (Stratagene). The clone containing the largest cDNA insert, pCGP489, was sequenced (SEQ ID No:2) and showed 88% similarity to the Petunia FLS genetic sequence at the nucleotide level, and 91% similarity over 241 amino acids to the Petunia FLS sequence encoded by pCGP481.

Construction and screening of a *Nicotiana sylvestris* cDNA library

A cDNA library in the vector λZAPII was made from RNA isolated from styles of *Nicotiana sylvestris* using methods described by Chen et al. (1992).

Approximately 120,000 cDNA clones were hybridised with $^{32}$P-labelled pCGP481 cDNA fragment in low stringency hybridisation buffer (6×SSC, 35% (v/v) formamide, 1% (w/v) SDS) for 16 hours at 42° C. The filters were washed in 2×SSC, 1% (w/v) SDS at 65° C. and then autoradiographed. Hybridising plaques were picked off into PSB to allow the phage to elute. Three plasmid clones were rescued using the single-stranded helper phage VCSM13. The clone containing the largest cDNA insert, pCGP490, was sequenced (SEQ ID No:3) and showed 84% similarity to the Petunia FLS genetic sequence at the nucleotide level, and 93% similarity over the 45 amino acid sequence to the Petunia FLS sequence encoded by pCGP481.

A comparison of the amino acid sequences of the two Nicotiana cDNA clones pCGP489 (SEQ ID No:2) and pCGP490 (SEQ ID No:3) with the amino acid sequence of the petunia FLS cDNA clone (SEQ ID No:1) is shown in Table 7, overleaf.

TABLE 7

COMPARISON OF SEQUENCES FROM *NICOTIANA* WITH pCGP481

```
                    70            80            90           100           110           120
                     *             *             *             *             *             *
PetFLS¹     R D P D E N K M V K L I A D A S K E WG I F Q L I N H G I P D E A I A D L Q K V G K E F F E H V P Q E E K E L I A K T P
pCGP489²                                                                              V P Q E E K E m I A K s P 130           140           150           160           170           180
                     *             *             *             *             *             *
PetFLS      G S N D I E G Y G T S L Q K E V E G K K G WV D H L F H K I WP P S A V N Y R Y WP K N P P S Y R E A N E E Y G K R M R
pCGP489     G S q n I E G Y G T S L Q K E V E G K r  G WV D H L F H K I WP P S A i  N Y R Y WP K N P P S Y R E A N E E Y a K R l  R
```

TABLE 7-continued

COMPARISON OF SEQUENCES FROM *NICOTIANA* WITH pCGP481

```
              190              200              210              220              230              240
               *                *                *                *                *                *
PetFLS    E V V D R I  F K S L S L G L G L E  G H E MI  E A A G G D E I  V Y L L KI  N Y Y P P  C P  R P  D L A L G V V A H T D M S  Y I
pCGP489   E Va e k mF K S L S L G L G L E a  H E MmE  A A G Ge d I  V Y L L KI  N Y Y P P  C P  R P  D L A L G V V A H T D M S  h I
          . . . .                              .         .          . .                                                        .

250              260              270              280              290              300
               *                *                *                *                *                *
PetFLS    T I  L V P  N E V Q G L Q V F  K D G H W Y D V K Y I  P N A L I  V H I  G D Q V E I  L S N G K Y K S  V Y H R T T V N K D K T R
pCGP489.  T I  L V P  N E V Q G L Q V F  K D G H W Y D Vn Y I  P N A L I  V H I  G D Q1 E I  L S N G K Y K S  V Y H R T T Vt  K D K T R 310              320              330              340
               *                *                *                *
PetFLS    M S  W P  V F L E P P  S E H E  V G P I  P K L L S  E A N P P  K F  K T K K Y K D Y V Y C K L N K L P  Q
pCGP489.  M S  W P  V F L E P P  S E H E  V G P I  P K L v n  E A N P P  K F  K T K K Y K D Y V Y C K L N K L P  Q pCGP490³           P  V F L E P P  S E H E  V G P I  s K L v n  E A N P P  K F  K T K K Y K D Y V Y C K L N K L P  Q
                                                       .  . .
```

[1] *Petunia* FLS amino acid sequence (SEQ ID No:1)
[2] *Nicotiana alata* sequence (SEQ ID No:2)
[3] *Nicotiana sylvestris* sequence (SEQ ID No:3)
. Amino acid mismatches in the compared sequences; all other amino acids are identical over the sequence lengths compared.

EXAMPLE 11

ISOLATION OF cDNA HOMOLOGUE FROM DIANTHUS

Construction of a Dianthus cDNA library

Total RNA was isolated from the petal tissue of *D. caryopihyllus* cv. Laguna stage 3 flowers, using the method of Turpen and Griffith (1986). Poly(A)⁺RNA was selected from the total RNA by Oligotex dT-30 (Takana, Japan) following the manufacturer's protocol.

cDNA was made and a library constructed in λZAPII according to the protocol used for the petunia library.

The primary library, which contained 150,000 pfu, was plated at 37,500 pfu per 15 cm diameter plate after transfecting E coli SURE cells. The plates were incubated at 37° C. for eight hours, then stored overnight at 4° C. Phage were eluted from the plates into phage storage buffer (8 mM MgSO$_4$, 100 mM NaCl, 0.01% (w/v) gelatin, 50 mM Tris-HCl, pH 8.0) to form an amplified cDNA library stock.

Isolation of a FLS homologue from a Dianthus cDNA, library

A total of 100,000 plaques were screened, in duplicate, with ³²P-labelled 1.1 kb EcoRI-HindII pDIOXC3 cDNA fragment (5×10⁵ cpm/μL). Hybridisation was carried out in a low stringency buffer (6×SSC, 0.5% (w/v) SDS, 5×Denhardt's solution, 0.01M EDTA, 100 μg/ml) for 16 hours at 42° C. The filters were washed in 2×SSC/1% (w/v) SDS at 65° C. and then autoradiographed. Hybridised cDNA clones were rescued from λZAPII using the single-stranded helper phage Exassist (Stratagene) according to the manufacturer's instructions.

When sequenced, one of the isolated clones, pCGP777 (SEQ ID No:4), revealed 65% similarity at both the nucleotide level and the amino acid level to the Petunia FLS sequence encoded by pCGP481.

EXAMPLE 12

ISOLATION OF cDNA HOMOLOGUE FROM CHRYSANTHEMUM

Construction of a Chrysanthemum cDNA library

Total RNA was isolated from the petal tissue of *Chrysanthemum morifolium* cv. Dark Pink Pompom (Reference Number 5999), stages 2 and 3 flowers, again using the method of Turpen and Griffith (1986). An amount of 30 μg of the total RNA was used as template for cDNA synthesis.

Following fractionation and ligation, the cDNA reaction mixture was packaged using the Packagene system (Promega). The titre of the unamplified library was 3.7×10⁴ pfu/ml.

Isolation of a FLS homologue from a Chrysanthemum cDNA library

An amount of 90,000 pfu (of amplified library; 2.6×10⁷ pfu/ml) of the packaged cDNA was plated at 10,000 pfu per 15 cm diameter plate after transfecting XL1-Blue cells. The plates were incubated at 37° C. overnight, then stored at 4° C. Duplicate lifts were taken onto Colony/Plaque Screen™ filters (DuPont), treated as recommended by the manufacturer, and screened with the ³²P-labelled EcoRI-XhoI pCGP481 cDNA fragment. Hybridisation was carried out in a low stringency buffer (6×SSC, 1.0% (w/v) SDS, 20% (v/v) formamide) for 16 hours at 42° C. The filters were washed twice for 30 minutes in 2×SSC/1% SDS at 65° C., and then autoradiographed.

The isolated clone pCGP874 (SEQ ID No:5), when sequenced, revealed 70% similarity at the nucleotide level and 72% similarity at the amino acid level to the Petunia FLS sequence encoded by pCGP481.

EXAMPLE 13

EXPRESSION OF PCGP874 cDNA IN YEAST

Construction of the yeast expression vector pYGA22m and pCGP492

The yeast expression vector pYGA22m was contructed as described in Example 8 above. A 1.3 kb EcoRI-XhoI fragment that included the entire cDNA insert from pCGP874 was ligated with the 9 kb EcoRI-SalI fragment from pYGA22m, in the same manner as for the construction of PCGP 631, described above and shown in FIG. 4. The resulting plasmid, designated pCGP492, contained the pCGP874 cDNA fragment ligated in a sense orientation behind the glyceraldehyde-3-phosphate dehydrogenase promoter.

Yeast transformation and assay of FLS activity

Transformation of yeast and preparation of extracts for assay of FLS activity were carried out as described above in Example 8. FLS activity was again measured by the method of Forkmann et al. (1986) with modifications, using unlabelled DHK and DHQ as substrates. The results confirmed that the pCGP874 cDNA encodes a functional chrysanthemum FLS enzyme.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

Ashikara, T., Kiuchi-Goto, N., Tanaka, Y., Shibano, Y., Amachi, T., and Yoshizumi, H. *AppL MicrobioL Biotechnol* 30: 515–520, 1989.

Aviv, H. and Leder, P. *Proc. Natl. Acai Sci. USA* 69: 1408, 1972.

Baird, W. V. and Meagher, R. B. *EMBO J.* 6: 3223–3231, 1987.

Bethesda Research Laboratories. BRL pUC host: E. coli DH5a™ competent cells. *Bethesda Res. Lab. Focus.* 8(2): 9, 1986.

Britsch, L., Heller, W. and Grisebach, H. *Z. Naturforsch.* 36c: 742–750, 1981.

Brugliera, F. et al. *The Plant Journal* (in press), 1993.

Bullock, W. O., Fernandez, J. M. and Short, J. M. *Biotechniques* 5: 376, 1987.

Chen, C. G., Cornish, E. C. and Clarke, A. E. The Plant Cell 4: 1053–1062, 1992.

Cohen, G., Shiffman, D., Mevarech, M. and Aharonowitz, Y. *TIBTECH* 8: 105–111, 1990.

Cornu, A., Farcy, E., Maizonnier, D., Haring, M., Veerman, W. and Gerats, A. G. M., In "Genetic maps—Locus maps of complex genomes." 5th edition, Stephen J. O'Brien (ed), Cold Spring Harbor Laboratory Press, USA, 1990.

Deikman, J. and Fischer, R. L. *EMBO J.* 7: 3315–3320, 1988.

Dellaporta. S. J., Wood, J. and Hick, J. B. *Plant Mol. Biol. Rep.* 1: 19–21, 1983.

Doodeman, M., Gerats, A. G. M., Schram, A. W., de Vlaming, P. and Bianchi, F. *Theor. Appl. Genet.* 67: 357–366, 1984.

Ebel, J. and Hahlbrock, K., In "The Flavonoids: Advances in Research Since 1980." Harborne, J. B. (ed), Academic Press, New York, USA, 641–679, 1988.

Forkmann, G. *Plant Breeding* 106: 1–26, 1991.

Forkmann, G., de Vlaming, P., Spribille, R., Wiering, H. and Schram, A. W. *Z. Naturforsch.* 41c: 179–186, 1986.

Gerats, A.G.M. "Mutable systems; their influence on flavonoid synthesis in *Petunia hybtida*." PhD Thesis, Free University, Amsterdam, 1985.

Gynheung, A. N., Ebert, P. R., Mitra, A. and Ita, S. B. Binary vectors. In "Plant Molecular Biology Manual.", Gelvin, S. B., Schilperoort, R. A., Verma, D. P. S. (eds), Kluwer Academic Publishers, Dordrecht, Belgium, A3: 1–19, 1988.

Hahlbrock, K. and Grisebach, H. *Annu. Rev. Plant PhysioL* 30: 105–130, 1979.

Hanahan, D. *J. Mol. Biol.* 166: 557, 1983.

Haseloff, J. and Gerlach, L. *Nature* 334: 586–591, 1988.

Higgins, D. G. and Sharp, P. M. *Gene* 73: 237–244, 1988.

Holdsworth, M. J., Bird, C. R., Ray, J., Schuch, W. and Grierson, D. *Nucleic Acids Research* 15: 731–739, 1987.

Horsch, R. B., Fry, J. E., Hoffmann, N. L., Eicholtz, D., Rogers, S. G. and Fraley, R. T. *Science* 227, 1229–1231, 1985.

Ito, H., Fukuda, Y., Murata, K. and Kimura, A. *J. Bacteriol* 153, 163–168, 1983.

Lazo, G. R., Pascal, A. S. and Ludwig, R. A. *Bio/Technology* 9: 963–967, 1991.

Martin, C., Prescott, A., Mackay, S., Bartlett, J. and Vrijlandt, E. *The Plant Journal* 1: 37–49, 1991.

Martin, F. M., Castro, N. M., Aboula-ela, F. and Tinoco, I. *Nucleic Acids Res.* 13: 8927–8938, 1985.

Maniatis, T., Fritsch, E. F. and Sambrook, J. "Molecular Cloning: A Laboratory Manual." Cold Spring Harbor Laboratory Press, USA, 1982.

Matsuda, J., Okabe, S., Hashimoto, T. and Yamada, Y. *J. Biol. Chem.* 266: 1–5, 1991.

Menssen, A., Hohmann, S., Martin, W., Schnable, P. S., Peterson, P. A., Saedler, H. and Gierl, A. *EMBO J.* 9: 3051–3057, 1990.

Merrifield, *J. Am Chem. Soc.* 85: 2149, 1964.

Mo, Y., Nagel, C. and Taylor, L. P. *Proc. Natl. Acad. Sci. USA* 89: 7213–7217, 1992.

Ohtsuka, E., Matsuki, S., Ikehara, M., Takahashi, Y. and Matsubara, K. *J. Biol. Chem.* 260: 2605–2608, 1985.

Sambrook, J., Fritsch, E. F. and Maniatis, T. "Molecular Cloning: A Laboratory Manual." (2nd edition), Cold Spring Harbor Laboratory Press, USA, 1989.

Sanger, F., Nicklen, S. and Coulson, A. *Proc. Natl. Acad. Sci. USA* 74: 5463–5467, 1977.

Schram, A. W., Jonsson, L.M.V. and Bennink, G. J. H. *Biochemistry of flavonoid synthesis in Petunia hybrida.* In "Petunia." Sink, K. C. (ed), Springer-Verlag, Berlin, Germany pp 68–75, 1984.

Scott-Moncrieff, R. J. *Genet.* 32: 117–170, 1936.

Spribille, R. and Forkrnann, G. *Z. Naturforsch.* 39c: 714–719, 1984.

Stafford, H. A. "Flavonoid Metabolism." CRC Press, Inc. Boca Raton, Fla., USA, 1990.

Sutter, A., Poulton, J. and Grisebach, H. *Arch. Biochem. Biophys.* 170: 547–556, 1975.

Turpen, T. H. and Griffith, O. M. *BioTechniques* 4: 11–15, 1986.

van Tunen, A. J., Gerats, A. G. M. and Mol, J. N. M. Plant MoL Biol. Rep. 8: 50–59, 1990.

Wallroth, M., Gerats, A. G. M., Rogers, S. G., Fraley, R. T. and Horsch, R. B. Mol. Gen. Genet. 202: 6–15, 1986.

Wiering, H., de Vlaming, P., Cornu, A and Maizonnier, D. Petunia genetics I—List of genes. *Ann. Amelior. Plant* 29: 611–622, 1979.

Wiering, H. and de Vlaming, P. *Inheritance and Biochemistry of Pigments.* In "Petunia" Sink, K. C. (ed), Springer-Verlag, Berlin, Germany pp 49–65, 1984.

Yoshitama, K., Ishikura, N., Fuleki, T. and Nakamura, S. *J. Plant Physiol.* 139: 513–518, 1992.

What is claimed is:

1. An isolated nucleic acid encoding or complementary to a sequence encoding a flavonol synthase (FLS), said sequence encoding a FLS comprising a nucleotide sequence as set forth in at least one of SEQ ID NOs:1–5 or a nucleotide sequence having at least 50% similarity to at least one of SEQ ID NOs:1–5.

2. An isolated nucleic acid molecule according to claim 1 wherein said nucleic acid is DNA.

3. An isolated nucleic acid molecule according to claim 1 or 2 wherein the plant is selected from the group consisting of petunia, snapdragon, tobacco, rose, carnation, chrysanthemum, lisianthus, cyclamen, parsley and grape.

4. An isolated nucleic acid molecule according to claim 3 wherein the plant is selected from the group consisting of petunia, tobacco, carnation and chrysanthemum.

5. An isolated nucleic acid molecule according to claim 4 having a nucleotide sequence or complementary nucleotide sequence which comprises the sequence as set forth in SEQ ID No:1 or having at least 50% similarity thereto.

6. An isolated nucleic acid molecule according to claim 4 having a nucleotide sequence or complementary nucleotide sequence which comprises the sequence as set forth in SEQ ID NO:2 or having at least 50% similarity thereto.

7. An isolated nucleic acid molecule according to claim 4 having a nucleotide sequence or complementary nucleotide sequence which comprises the sequence as set forth in SEQ ID No:3 or having at least 50% similarity thereto.

8. An isolated nucleic acid molecule according to claim 4 having a nucleotide sequence or complementary nucleotide sequence which comprises the sequence as set forth in SEQ ID NO:4 or having at least 50% similarity thereto.

9. An isolated nucleic acid molecule according to claim 4 having a nucleotide sequence or complementary nucleotide sequence which comprises the sequence as set forth in SEQ ID No:5 or having at least 50% similarity thereto.

10. An isolated DNA molecule comprising a sequence of nucleotides which
    (i) encodes a FLS of plant origin; and
    (ii) has at least 50% nucleotide sequence similarity to the sequence set forth in SEQ ID No:1.

11. An isolated DNA molecule according to claim 10 having a nucleotide sequence as set forth in SEQ ID NO:1.

12. An isolated DNA molecule according to claim 10 having a nucleotide sequence as set forth in SEQ ID NO:2.

13. An isolated DNA molecule according to claim 10 having a nucleotide sequence as set forth in SEQ ID NO:3.

14. An isolated DNA molecule according to claim 10 having a nucleotide sequence as set forth in SEQ ID No:4.

15. An isolated DNA molecule according to claim 10 having a nucleotide sequence as set forth in SEQ ID NO:5.

16. An isolated nucleic acid molecule which:
    (i) encodes a FLS of plant origin; and
    (ii) hybridizes under low stringency conditions to the nucleotide sequence set forth in SEQ ID NO:1 or to a complementary strand thereof.

17. An isolated nucleic acid molecule according to claim 16 having a nucleotide sequence as set forth in SEQ ID NO:1.

18. An isolated nucleic acid molecule according to claim 16 having a nucleotide sequence as set forth in SEQ ID NO:2.

19. An isolated nucleic acid molecule according to claim 16 having a nucleotide sequence as set forth in SEQ ID NO:3.

20. An isolated nucleic acid molecule according to claim 16 having a nucleotide sequence as set forth in SEQ ID NO:4.

21. An isolated nucleic acid molecule according to claim 16 having a nucleotide sequence as set forth in SEQ ID NO:5.

22. A vector comprising the nucleic acid molecule according to at least one of claims 1, 10, or 16.

23. A vector according to claim 22 wherein the nucleic acid molecule is operably linked to a promoter.

24. A vector according to claim 23 capable of replication and expression in a eukaryotic cell.

25. A vector according to claim 23 capable of replication and expression in a prokaryotic cell.

26. A transgenic plant carrying a non-indigenous genetic sequence encoding a FLS.

27. A transgenic plant according to claim 26 wherein the genetic sequence is capable of expression and said expression is optionally regulatable.

28. A transgenic plant according to claim 27 wherein the expression is developmentally regulated.

29. A transgenic plant according to claim 26 or 27 wherein the FLS is from a plant selected from the group consisting of petunia, snapdragon, tobacco, rose, carnation, chrysanthemum, lisianthus, cyclamen, parsley and grape.

30. A transgenic plant according to claim 26 or 27 wherein the FLS is from a plant selected from the group consisting of petunia, tobacco, carnation and chrysanthemum.

31. A transgenic plant according to claim 26 or 27 wherein said plant is selected from the group consisting of petunia, rose, carnation, chrysanthemum, gerbera, tobacco, lisianthus, lily, iris and pelargonium.

32. A transgenic plant according to claim 26 or 27 wherein the FLS is encoded by a nucleotide sequence as set forth in SEQ ID No:1 or having at least 50% similarity thereto.

33. A transgenic plant according to claim 26 or 27 wherein the FLS is encoded by a nucleotide sequence as set forth in SEQ ID NO:2 or having at least 50% similarity thereto.

34. A transgenic plant according to claim 26 or 27 wherein the FLS is encoded by a nucleotide sequence as set forth in SEQ ID No:3 or having at least 50% similarity thereto.

35. A transgenic plant according to claim 26 or 27 wherein the FLS is encoded by a nucleotide sequence as set forth in SEQ ID No:4 or having at least 50% similarity thereto.

36. A transgenic plant according to claim 26 or 27 wherein the FLS is encoded by a nucleotide sequence as set forth in SEQ ID No:5 or having at least 50% similarity thereto.

37. A transgenic plant consisting of at least one of petunia, rose, carnation, chrysanthemum, gerbera, tobacco, lisianthus, lily, iris or pelargonium carrying a non-indigenous genetic sequence encoding a FLS, said genetic sequence capable of being expressed in said plant and wherein said FLS is encoded by a DNA molecule comprising a DNA strand capable of hybridising under low stringency conditions to a nucleic acid molecule comprising the sequence of nucleotides set forth in at least one of SEQ ID NO:1, SEQ ID NO:2, SEQ ID NO:3, SEQ ID NO:4 or SEQ ID NO:5 or a nucleotide sequence having at least 50% sequence similarity to at least one of SEQ ID NO:1, SEQ ID NO:2, SEQ ID NO:3, SEQ ID NO:4, or SEQ ID NO:5.

38. A method for producing a transgenic flowering plant capable of exhibiting altered flower color, said method comprising introducing into a cell of a suitable plant the nucleic acid molecule according to at least one of claims 1, 10, or 16 regenerating a transgenic plant from the cell and growing said transgenic plant for a time and under conditions sufficient to permit expression of the nucleic acid sequence into FLS.

39. A method according to claim 38 wherein the transgenic plant is selected from the group consisting of petunia, rose, carnation, chrysanthemum, gerbera, tobacco, lisianthus, lily, iris and pelargonium.

40. A method according to claim 39 wherein the introduced nucleic acid is DNA and encodes FLS having the nucleotide sequence as set forth in at least one of SEQ ID NO:1, SEQ ID NO:2, SEQ ID NO:3, SEQ ID NO:4 or SEQ ID NO:5.

41. A method for producing a transgenic flowering plant capable of exhibiting altered flower color, said method comprising introducing into a cell of a plant carrying an indigenous FLS, the nucleic acid according to at least one of claims 1, 10, or 16 under conditions to induce co-suppression of said indigenous FLS.

42. A method according to claim 41 wherein the transgenic plant is selected from the list consisting of petunia, rose, carnation, chrysanthemum, gerbera, tobacco, lisianthus, lily, iris and pelargonium.

43. A method according to claim 42 wherein the introduced nucleic acid is DNA and encodes FLS and has the nucleotide sequence as set forth in at least one of SEQ ID NO:1, SEQ ID NO:2, SEQ ID NO:3, SEQ ID NO:4 or SEQ ID NO: 5.

* * * * *

UNITED STATES PATENT AND TRADEMARK OFFICE
CERTIFICATE OF CORRECTION

PATENT NO. : 5,859,329
DATED : January 12, 1999
INVENTOR(S) : Timothy A. Holton, et al.

It is certified that error appears in the above-identified patent and that said Letters Patent are hereby corrected as shown below:

Column 4, Line 9: "plant An" should read --plant. An--
Column 5, Line 21: "ac ids" should read --acids--
Column 5, Line 55: "snore" should read --more--
Column 10, Line 55: Delete --In the Figures--
Column 11, Line 33: "Eschetichia" should read --Escherichia--
Column 11, Line 33: "strins" should read --strains--
Column 12, Line 62: "AIITTI" should read --AIITI--
Column 13, Line 2: "dithiothireitol" should read --dithiothreitol--
Column 14, Line 39: "$_nYP_pCP_qP$" should read --$_nYP_pCP_qP$--
Column 15, Line 5: "KCI" should read --KCl--
Column 23, Line 21 and 22: "AppL MicrobioL BiotechnoL" should read --Appl Microbiol Biotechnol--
Column 23, Line 24: "Acai" should read --Acad.--
Column 23, Line 58: "hybtida" should read --hybrida--
Column 24, Line 1: "physioL" should read --physiol.--
Column 24, Line 45: "Forkrnann" should read --Forkmann--
Column 24, Line 54: "MoL" should read --Mol--

Signed and Sealed this

First Day of May, 2001

Attest:

NICHOLAS P. GODICI

Attesting Officer

Acting Director of the United States Patent and Trademark Office